US009034576B2

(12) United States Patent
Smilansky et al.

(10) Patent No.: US 9,034,576 B2
(45) Date of Patent: May 19, 2015

(54) SYSTEMS AND METHODS FOR MEASURING TRANSLATION OF TARGET PROTEINS IN CELLS

(75) Inventors: Zeev Smilansky, M.P. Emek Soreq (IL); Barry S. Cooperman, Penn Valley, PA (US); Yale E. Goodman, Merion, PA (US)

(73) Assignee: ANIMA CELL METROLOGY INC., Bernardsville, NJ (US)

( * ) Notice: Subject to any disclaimer, the term of this patent is extended or adjusted under 35 U.S.C. 154(b) by 388 days.

(21) Appl. No.: 13/497,273

(22) PCT Filed: Sep. 21, 2010

(86) PCT No.: PCT/IL2010/000792
§ 371 (c)(1),
(2), (4) Date: Mar. 21, 2012

(87) PCT Pub. No.: WO2011/036666
PCT Pub. Date: Mar. 31, 2011

(65) Prior Publication Data
US 2012/0183957 A1   Jul. 19, 2012

Related U.S. Application Data

(60) Provisional application No. 61/245,313, filed on Sep. 24, 2009.

(51) Int. Cl.
*C12Q 1/68*   (2006.01)
*G01N 33/50*   (2006.01)
*G01N 33/542*   (2006.01)

(52) U.S. Cl.
CPC .......... *G01N 33/5023* (2013.01); *G01N 33/542* (2013.01)

(58) Field of Classification Search
None
See application file for complete search history.

(56) References Cited

U.S. PATENT DOCUMENTS

| | | |
|---|---|---|
| 5,082,767 A | 1/1992 | Hatfield |
| 5,626,058 A | 5/1997 | Karpowich |
| 5,643,722 A | 7/1997 | Rothschild |
| 5,706,498 A | 1/1998 | Fujimiya |
| 5,777,079 A | 7/1998 | Tsien |
| 5,856,928 A | 1/1999 | Yan |
| 5,922,858 A | 7/1999 | Rothschild |
| 6,189,013 B1 | 2/2001 | Maslyn |
| 6,210,941 B1 | 4/2001 | Rothchild |
| 7,015,486 B1 | 3/2006 | Sarbach |
| 7,288,372 B2 | 10/2007 | Olejnik |
| 7,388,125 B2 | 6/2008 | Ristic |
| 2003/0092031 A1 | 5/2003 | Rothchild |
| 2003/0219780 A1 | 11/2003 | Olejnik |
| 2003/0219783 A1 | 11/2003 | Puglisi |
| 2004/0023256 A1 | 2/2004 | Puglisi |
| 2004/0023874 A1 | 2/2004 | Burgess |
| 2004/0235175 A1 | 11/2004 | Gaudernack |
| 2005/0118151 A1 | 6/2005 | Larsen |
| 2005/0157294 A1 | 7/2005 | Hopkins |
| 2005/0164264 A1 | 7/2005 | Shipwash |
| 2005/0267037 A1 | 12/2005 | Anderson |
| 2006/0228708 A1 | 10/2006 | Smilansky |
| 2006/0292566 A1 | 12/2006 | Frazer |
| 2007/0021597 A1 | 1/2007 | Edwards |
| 2007/0134814 A1 | 6/2007 | Kajander |
| 2009/0081643 A1 | 3/2009 | Preminger |
| 2010/0267030 A1* | 10/2010 | Smilansky ........................ 435/6 |
| 2010/0317121 A1 | 12/2010 | Smilansky |
| 2011/0262899 A1 | 10/2011 | Cooperman |

FOREIGN PATENT DOCUMENTS

| | | |
|---|---|---|
| DE | 4410655 | 9/1995 |
| EP | 1428016 | 6/2004 |
| FR | 2798143 | 3/2001 |
| WO | 94/02595 A1 | 2/1994 |
| WO | 2001/016375 | 3/2001 |
| WO | 03/002554 A1 | 3/2003 |
| WO | 03/052067 A1 | 6/2003 |
| WO | 03/057164 A1 | 7/2003 |
| WO | 2003/064604 | 8/2003 |
| WO | 2004/050825 A1 | 6/2004 |
| WO | 2005/001062 A1 | 1/2005 |
| WO | 2005/116252 A1 | 8/2005 |
| WO | 2007/002758 | 1/2007 |
| WO | 2008/028298 | 3/2008 |
| WO | 2009/047760 | 4/2009 |

OTHER PUBLICATIONS

Funatsu et al., (1995) Imaging of single fluorescent molecules and individual ATP turnovers by single myosin molecules in aqueous solution. Nature 374(6522): 555-9.

Huang and Cantor (1975) Studies of 30 S *Escherichia coli* ribosome reassembly using individual proteins labeled with an environmentally sensitive fluorescent probe. J Mol Biol 97(4): 423-441.

Humphery-Smith et al., (1997) Proteome research: complementarity and limitations with respect to the RNA and DNA worlds. Electrophoresis 18(8): 1217-42.

Langlois et al., (1975) A comparison of the fluorescence of the Y base of yeast tRNA-Phe in solution and in crystals. Biochemistry 14(11): 2554-8.

(Continued)

*Primary Examiner* — Nancy T Vogel

(74) *Attorney, Agent, or Firm* — Roach Brown McCarthy & Gruber, P.C.; Kevin D. McCarthy

(57) ABSTRACT

The present invention relates to systems and methods for measuring the rate of translation of a target protein in cells, which are based on the detection of translation of one or more predetermined codon pairs during synthesis of the target protein. The detection is provided by a FRET signal emitted from labeled tRNA molecules which are juxtaposed during synthesis of the protein.

19 Claims, 6 Drawing Sheets

(56) References Cited

OTHER PUBLICATIONS

Nyborg and Liljas (1998) Protein biosynthesis: structural studies of the elongation cycle. FEBS Lett 430(1-2): 95-9.

Ramakrishnan (2002) Ribosome structure and the mechanism of translation. Cell 108(4): 557-72.

Schlünzen et al., (2001) Structural basis for the interaction of antibiotics with the peptidyl transferase centre in eubacteria. Nature 413(6858): 814-21.

Yates (1998) Database searching using mass spectrometry data. Electrophoresis 19(6): 893-900.

Agrawal, Rajendra K et al, (2007) Visualization of tRNA Movements on the Escherichia coli 70s Ribosome during the Elongation Cycl. J Cell Biol 150(3):447-460.

Akhtar, Saghir and Juliano, R. L. (1992) Cellular uptake and intracellular fate of antisense oligonucleotides.Trends Cell Bio. 2(5):139-144.

Bianchi, G et al., (2009) The proteasome load versus capacity balance determines apoptotic sensitivity of multiple myeloma cells to proteasome inhibition. Blood 26 vol. 113(13):3040-3049.

Blanchard, Scott C. et al., (2004) tRNA selection and kinetic proofreading in translation. Nat Struct Mol Biol 11(10):1008-1014.

Bush, Kevin T. et al., (1997) Proteasome inhibition leads to a heat-shock response, induction of endoplasmic reticulum chaperones, and thermotolerance. J Biol Chem 272(14):9086-9092.

Calvo, Sarah E. et al., (2009) Upstream open reading frames cause widespread reduction of protein expression and are polymorphic among humans. Proc Natl Acad Sci U.S.A. 106(18)7507-7512.

Caplan, Arnold I., (2007) Adult mesenchymal stem cells for tissue engineering versus regenerative medicine. J Cell Physiol 213(2):341-347.

Felgner, Philip L. et al., (1987) Lipofection: a highly efficient, lipid-mediated DNA-transfection procedure. Proc Natl Acad Sci U.S.A. 84(21):7413-7417.

Fribley, Andrew and Wang, Cun-Yo (2006) Proteasome inhibitor induces apoptosis through induction of endoplasmic reticulum stress. Cancer Biol Ther 5(7):745-748.

Glenn, Jeffrey S. et al., (1993) Delivery of liposome-encapsulated RNA to cells expressing influenza virus hemagglutinin. Methods Enzymol 221:327-339.

Graf, Ralph et al., (2005) Live cell spinning disk microscopy. Adv Biochem Eng Biotechnol 95:57-75.

Hanley, Q. S. et al., (1999) An optical sectioning programmable array microscope implemented with a digital micromirror device. J Microsc 196:317-331.

Harousseau, Jean-Luc et al., (2005) Stem-cell transplantation in multiple myeloma. Best Pract Res Clin Haematol 18(4):603-618.

Helmchen, Fritjof and Denk, Winfried (2005) Deep tissue two-photon microscopy. Nat Methods 2(12):932-940.

Jemal, Ahmedin et al., (2008) Cancer statistics. CA Cancer J Clin 58(2):71-96.

Jia, Yiwei et al., (1997) Nonexponential kinetics of a single tRNAPhe molecule under physiological conditions. Proc Natl Acad Sci USA 94(15):7932-7936.

Johnson, Arthur E. (2005) The co-translational folding and interactions of nascent protein chains: a new approach using fluorescence resonance energy transfer. FEBS Lett 579(4):916-920.

Jun, Soo Youn et al., (2008) Fluorescent labeling of cell-free synthesized proteins with fluorophore-conjugated methionylated tRNA derived from in vitro transcribed tRNA. J Microbiol Methods 73(3):247-251.

Kapp, Lee D. and Lorsch, Jon R. (2004) The molecular mechanics of eukaryotic translation. Annu Rev Biochem. 73:657-704.

Kochetov, Alex V. et al., (1998) Eukaryotic mRNAs encoding abundant and scarce proteins are statistically dissimilar in many structural features. FEBS Lett 440(3):351-355.

Kumar, Shaji K. et al., (2008) Improved survival in multiple myeloma and the impact of novel therapies. Blood 111(5):2516-2520.

Liu, Wei-Yi et al., (2005) Efficient RNA interference in zebrafish embryos using siRNA synthesized with SP6 RNA polymerase. Dev Growth Differ. 47(5):323-331.

Lu, D. et al., (1994) Optimization of methods to achieve mRNA-mediated transfection of tumor cells in vitro and in vivo employing cationic liposome vectors. Cancer Gene Ther 1:245-252.

Malone, Robert W. et al., (1989) Cationic liposome-mediated RNA transfection. Proc Natl Acad Sci USA. 86(16):6077-6081.

Olejnik, Jerzy et al., (2005) N-terminal labeling of proteins using initiator tRNA. Methods 36(3):252-260.

Rae, James L. and Levis, Richard A. (2002) Single-cell electroporation. Pflugers Arch 443(4):664-670.

Rodnina, Marina V. et al., (2005) Recognition and selection of tRNA in translation. FEBS Letters 579(4):938-942.

Sakamoto, T. et al., (2004) Improvement of dermatitis by iontophoretically delivered antisense oligonucleotides for interleukin-10 in NC/Nga mice. Gene Ther 11(3):317-324.

Sako, Yusuke et al., (2006) A novel therapeutic approach for genetic diseases by introduction of suppressor tRNA. Nucleic Acids Symp Ser (Oxf) 50:239-240.

Sako, Yusushi and Yanagida, Toshio (2003) Single-molecule visualization in cell biology. Nat Rev Mol Cell Biol 4 (Suppl):SS1-SS5.

Seibel, Peter et al., (1995) Transfection of mitochondria: strategy towards a gene therapy of mitochondrial DNA diseases. Nucleic Acids Res 23(1):10-17.

Soto-Gutierrez, Alejandro et al., (2008) Endoderm induction for hepatic and pancreatic differentiation of ES cells. Acta Med Okayama 62(2):63-68.

Szöllosi, Janos et al., (1998) Application of fluorescence resonance energy transfer in the clinical laboratory: routine and research. Cytometry 34(4):159-179.

Vestweber, Dietmar and Schatz, Gottfried (1989) DNA-protein conjugates can enter mitochondria via the protein import pathway. Nature 338(6211):170-172.

Watson, Bonnie S. et al., (1995) Macromolecular arrangement in the aminoacyl-tRNA.elongation factor Tu.GTP ternary complex. A fluorescence energy transfer study. Biochemistry 34(24):7904-7912.

Welch, Ellen M. et al., (2007) PTC124 targets genetic disorders caused by nonsense mutations. Nature 447 (7140):87-91.

Wintermeyer, W. and Zachau, H. G. (1971) Replacement of Y base, dihydrouracil, and 7-methylguanine in tRNA by artificial odd bases. FEBS Lett 18(2):214-218.

Yokoo, T. et al, (2008) Generation of a transplantable erythropoietin-producer derived from human mesenchymal stem cells. Transplantation 85(11):1654-1658.

Agmon (2003) On peptide bond formation, translocation, nascent protein progression and the regulatory properties of ribosomes. Derived on Oct. 20, 2002 at the 28th FEBS Meeting in Istanbul. Eur J Biochem 270(12):2543-2556.

Amann et al., (1995) Phylogenetic identification and in situ detection of individual microbial cells without cultivation. Microbiol Rev 59(1): 143-169.

Bakin et al., (1991) Spatial organization of template polynucleotides on the ribosome determined by fluorescence methods. J Mol Biol. 221(2):441-453.

Barhoom et al., (2011) Quantitative single cell monitoring of protein synthesis at subcellular resolution using fluorescently labeled tRNA. Nucleic Acids Res 39(19): e129.

Barhoom et al., (2013) Dicodon monitoring of protein synthesis (DiCoMPS) reveals novel levels of synthesis of a viral protein in single cells. Nucleic Acids Res pp. 1-10.

Behrens et al., (2003) Is the in situ accessibility of the 16S rRNA of Escherichia coli for Cy3-labeled oligonucleotide probes predicted by a three-dimensional structure model of the 30S ribosomal subunit? Appl Environ Microbiol 69(8): 4935-4941.

Bevan et al., (1995) Identifying small-molecule lead compounds: the screening approach to drug discovery. Trends Biotechnol 13(3): 115-121.

Brady PS and Brady LJ (1987) Hepatic carnitine palmitoyltransferase turnover and translation rates in fed, starved, streptozotocin-diabetic and diethylhexyl phthalate-treated rats. Biochem J 246(3): 641-649.

Braslaysky et al., (2003) Sequence information can be obtained from single DNA molecules. Proc Natl Acad Sci USA 100(7):3960-3964.

(56) References Cited

OTHER PUBLICATIONS

Chang et al., (2006-2007) Significance of molecular signaling for protein translation control in neurodegenerative diseases. Neurosignals 15(5): 249-258.

Cload et al., (1996) Development of improved tRNAs for in vitro biosynthesis of proteins containing unnatural amino acids. Chem Biol. 3(12):1033-1038.

Cooperman BS (1988) Affinity labeling of ribosomes. Methods Enzymol 164: 341-361.

Cooperman et al., (2000) Photolabile derivatives of oligonucleotides as probes of ribosomal structure. Methods Enzymol 318: 118-136.

De Angelis (1999) Why FRET over genomics? Physiol Genomics 1(2):93-99.

Dittmar et al., (2005) Selective charging of tRNA isoacceptors induced by amino-acid starvation. EMBO Rep 6(2): 151-7.

Erdogan et al., (2001) Detection of mitochondrial single nucleotide polymorphisms using a primer elongation reaction on oligonucleotide microarrays. Nucleic Acids Res 29(7): E36.

Ermolaeva (2001) Synonymous codon usage in bacteria. Curr Issues Mol Biol 3(4): 91-7.

Fuchs et al., (1998) Flow cytometric analysis of the in situ accessibility of *Escherichia coli* 16S rRNA for fluorescently labeled oligonucleotide probes. Appl Environ Microbiol 64(12): 4973-4982.

Fuchs et al., (2001) In situ accessibility of *Escherichia coli* 23S rRNA to fluorescently labeled oligonucleotide probes. Appl Environ Microbiol 67(2): 961-968.

Ha (2001) Single-Molecule FRET. Single Molecules 2(4):283-4.

Hainrichson et al., (2007) Designer aminoglycosides: the race to develop improved antibiotics and compounds for the treatment of human genetic diseases. Org Biomol Chem 6(2): 227-39.

Heinze et al., (2000) Simultaneous two-photon excitation of distinct labels for dual-color fluorescence crosscorrelation analysis. Proc Natl Acad Sci USA 97(19):10377-10382.

Hobohm et al., (1984) Is the orcadian clock of gonyaulax held stationary after a strong pulse of anisomycin? Comparative Biochemistry and Physiology Part A: Physiology 79(3): 371-378.

Kukhanova et al., (1974) Peptidyl-tRNA with a fluorescent label: ribosome substrates in peptide bond formation. Mol Biol rep 1: 397-400.

Lee et al., (2010) Single-molecule four-color FRET. Angew Chem Int Ed 49: 9922-9925.

Loy et al., (2003) probeBase: an online resource for rRNA-targeted oligonucleotide probes. Nucleic Acids Res 31(1): 514-516.

Magde et al., (1974) Fluorescence correlation spectroscopy. II. An experimental realization. Biopolymers 13(1): 29-61.

Mhlanga and Tyagi (2006) Using tRNA-linked molecular beacons to image cytoplasmic mRNAs in live cells. Nat Protoc 1(3): 1392-8.

Miyawaki et al., (2003) Lighting up cells: labelling proteins with fluorophores. Nat Cell Biol Suppl: S1-7.

Monahan (2004) Chapter 3 The HSAS Assay: Optimizing tRNA Delivery to Mammalian Cells, In: The Development of a Mammalian Cell Expression System for Unnatural Amino Acid incorporation into Proteins. Thesis Caltech, 19 pages.

Monahan et al., (2003) Site-specific incorporation of unnatural amino acids into receptors expressed in Mammalian cells. Chem Biol 10(6): 573-80.

Muralikrishna P and Cooperman BS (1994) A photolabile oligodeoxyribonucleotide probe of the decoding site in the small subunit of the *Escherichia coli* ribosome: identification of neighboring ribosomal components. Biochemistry 33(6): 1392-1398.

Negrutskii and Deutscher (1991) Channeling of aminoacyl-tRNA for protein synthesis in vivo. Proc Natl Acad Sci U S A 88(11): 4991-4995.

Negrutskii et al., (1994) Supramolecular organization of the mammalian translation system. Proc Natl Acad Sci U S A 91(3): 964-8.

Paulsen et al., (1983) Topological arrangement of two transfer RNAs on the ribosome. Fluorescence energy transfer measurements between A and P site-bound tRNAphe. J Mol Biol 167(2): 411-426.

Robbins and Hardesty (1983) Comparison of ribosomal entry and acceptor transfer ribonucleic acid binding sites on *Escherichia coli* 70S ribosomes. Fluorescence energy transfer measurements from Phe-tRNAPhe to the 3' end of 16S ribonucleic acid. Biochemistry 22(24): 5675-5679.

Sako and Yanagida (2002) Total internal reflection fluorescence microscopy for single-molecule imaging in living cells. Cell Struct Funct. 27(5):357-365.

Schwille et al., (1999) Molecular dynamics in living cells observed by fluorescence correlation spectroscopy with one-and two-photon excitation. Biophys J 77(4): 2251-2265.

Sei-Iida et al., (2000) Real-time monitoring of in vitro transcriptional RNA synthesis using fluorescence resonance energy transfer. Nucleic Acids Research 28(12):e59.

Shen-Orr et al., (2002) Network motifs in the transcriptional regulation network of *Escherichia coli*. Nat Genet 31(1): 64-68.

Singh et al., (1999) Rapid kinetic characterization of hammerhead ribozymes by real-time monitoring of fluorescence resonance energy transfer (FRET). RNA 5(10):1348-56.

Smilansky (2001) Automatic registration for images of two-dimensional protein gels. Electrophoresis 22(9):1616-1626.

Sofia et al., (1998) Poly(ethylene oxide) Grafted to Silicon Surfaces: Grafting Density and Protein Adsorption. Macromolecules 31: 5059-5070.

Stapulionis R and Deutscher MP (1995) A channeled tRNA cycle during mammalian protein synthesis. Proc Natl Acad Sci U S A 92(16): 7158-7161.

Tsuji et al., (2000) Direct Observation of Specific Messenger RNA in a Single Living Cell under a Fluorescence Microscope. Biophysical Journal 78: 3260-3274.

Vukojević et al., (2005) Study of molecular events in cells by fluorescence correlation spectroscopy. Cell Mol Life Sci 62(5): 535-550.

Wiseman and Petersen (1999) Image correlation spectroscopy. II. Optimization for ultrasensitive detection of preexisting platelet-derived growth factor-beta receptor oligomers on intact cells. Biophys J 76(2): 963-977.

\* cited by examiner

SYSTEMS AND METHODS FOR MEASURING TRANSLATION OF TARGET PROTEINS IN CELLS

REFERENCE TO CO-PENDING APPLICATIONS

Priority to claimed as a 371 of international application number PCT/IL2010/000792, filed on Sep. 21, 2010; which claims priority to U.S. Provisional Patent application Ser. No. 61/245,313, filed on Sep. 24, 2009.

FIELD OF THE INVENTION

The present invention relates to systems and methods for measuring the rate of translation of a target protein in cells, which are based on the detection of translation of one or more predetermined codon pairs during synthesis of the target protein. The detection is provided by a FRET signal emitted from labeled tRNA molecules which are juxtaposed during synthesis of the protein.

BACKGROUND OF THE INVENTION

The Process of Protein Synthesis

Protein synthesis is one of the most central life processes. A protein is formed by the linkage of multiple amino acids via peptide bonds, according to a sequence defined by the template messenger RNA (mRNA). Protein synthesis occurs in the ribosomes, the protein manufacturing plants of every organism and nearly every cell type.

Ribosomes are ribonucleoprotein particles consisting of a small and large subunit. In bacteria these subunits have sedimentation coefficients of 30 and 50, and thus are referred to as "30S" and "50S" respectively; in eukaryotes the sedimentation coefficients are 40 and 60. The translation system makes use of a large number of components, including inter alia the ribosome, initiation, elongation, termination and recycling factors, transfer RNA, amino acids, aminoacyl synthetases, magnesium, and the product polypeptides.

Aminoacylated tRNAs read codons in ribosome-bound messenger RNAs and transfer their attached amino acids to growing peptide chains. The tRNA molecule has 73-93 nucleosides arranged in a cloverleaf-like structure, and includes the elements of an acceptor stem, a D-loop, an anticodon loop, a variable loop and a TψC loop. Aminoacylation, or charging, of tRNA results in linking the carboxyl terminal of an amino acid to the 2'-(or 3'-) hydroxyl group of a terminal adenosine base via an ester linkage. Aminoacylation occurs in two steps, amino acid activation (i.e. adenylation of the amino acid to produce aminoacyl-AMP), tRNA aminoacylation (i.e. attachment of an amino acid to the tRNA).

In most species, multiple tRNA molecules exist which become aminoacylated with the same amino acid but have different anticodon sequences. Such families of tRNAs are termed isoacceptors. There are 21 isoacceptor families, corresponding to 20 for the standard amino acids and one for seleno-cysteine. A particular tRNA may be denoted according to its aminoacylating amino acid, also referred to as its cognate amino acid, which is indicated in superscript such as in $tRNA^{Leu}$. A particular tRNA may further be denoted according to its anticodon, indicated in parentheses, such as $tRNA^{Leu}$ (CAG).

According to the genetic code, the total possible number of anticodons is 64, meaning that 61 different tRNA species (minus the stop codons) are theoretically required for translation. However, in most organisms the total number of tRNA species is generally less than this. This is due to the fact that at least some tRNAs are capable of reading (or "decoding") different codons that encode the same amino acid. For example, E. coli has five $tRNA^{Leu}$ isoacceptors that decode the six leucine codons, and four $tRNA^{Arg}$ isoacceptors that decode the six arginine codons. Distinct codons that encode the same amino acid are termed "synonymous" codons. Synonymous codons which differ only at the third base may often be read by the same tRNA due to "wobble" pairing. Wobble pairing is base pairing between a codon and an anticodon that does not obey the standard Watson-Crick pairing at the wobble position.

Protein translation, also referred to as "polypeptide synthesis," involves the stages of initiation, elongation and termination. The initiation stage begins by formation of the initiation complex, composed of the two ribosomal subunits, protein initiation factors, mRNA, and an initiator tRNA, which recognizes the initiator codon UAG of open reading frames. Elongation proceeds with repeated cycles of charged tRNAs binding to the ribosome (a step termed "recognition"), peptide bond formation, and translocation, involving elongation factors and enzymes such as peptidyl transferase, which catalyzes addition of amino acid moieties onto the growing chain. Termination factors recognize a stop signal, such as the base sequence UGA, in the mRNA, terminating polypeptide synthesis and releasing the polypeptide chain and mRNA from the ribosome. Recycling factor enables dissociation of the ribosome subunits, which are then available for a new round of protein synthesis (see for example, Kapp et al., 2004, Annu Rev Biochem. 73:657-704). In eukaryotes, ribosomes are often attached to the membranes of the endoplasmic reticulum (ER) and Golgi compartments. Additionally, ribosomes are active in organelles such as mitochondria and, in plant cells, in chloroplasts, and in other subcellular compartments. One important locus of protein synthesis activity is in dendritic spines of neurons.

Stem Cell-Based Therapies for Congenital Diseases

Stem cells and stromal cells of various types are currently in development for potential use in cell therapy for a wide variety of congenital diseases involving a deficiency of one or more proteins involved in normal growth or metabolism. Such proteins include insulin, growth factors, and erythropoietin, among many others. Stem and stromal cell populations that secrete such proteins in therapeutic qualities are urgently sought after, as described for example in Soto-Gutierrez A et al, Acta Med Okayama. 2008 April; 62(2):63-8; and in Yokoo T et al, Transplantation. 2008 Jun. 15; 85(11):1654-8. Methods for monitoring production of the target protein from stem cell candidates are critical to the development of such therapies.

In addition, stem and stromal cells have great potential in regenerative therapy for a wide variety of disorders, as described in Caplan A I., Adult mesenchymal stem cells for tissue engineering versus regenerative medicine. J Cell Physiol. 2007 November; 213(2):341-7. In order to monitor differentiation of stem and stromal cells into the desired cell types, it is important to be able to measure production of specialization and differentiation markers and factors at the protein translation level.

Use of Cells for Antibody Production

Cultured cells are widely used for production of recombinant antibodies for various therapeutic uses. In order to optimize antibody production, it is important to be able to measure antibody production at the protein translation level.

Fast and efficient methods for measuring translation of a particular protein of interest in real time are particularly useful in the above applications relating to stem cells and antibody production.

Diseases Related to Protein Translation

Control of protein translation is implicated in a large number of diseases. For example, the family of central nervous system (CNS) disorders connected with protein synthesis disturbances in neural spines. The family includes fragile X mental retardation, autism, aging and memory degeneration disorders such as Alzheimer's disease. Neural spines and synapses contain their own protein synthesis machinery. Synaptic plasticity, underpinning the most basic neural functions of memory and learning, is dependent upon proper regulation of spinal protein synthesis. Another important family of diseases directly connected to protein synthesis includes genetic disorders associated with the presence of premature termination codons (PTC) in the coding sequence of a critical protein, preventing its translation. Such diseases include Duchenne Muscular Dystrophy and a large family of congenital diseases. A small molecule known as PTC124 (Welch E M et al, Nature 2007 May 3; 447(7140):87-91) helps the ribosome slide over the mutated codon, thereby producing the required protein, albeit at only at 1-5% of normal concentrations. These amounts are often sufficient to sustain the life of an afflicted individual. PTC suppression has also been achieved by introducing charged suppressor tRNA into a living cell, enabling readthrough suppression of the PTC-containing mRNA and accumulation of the encoded protein (Sako et al, Nucleic Acids Symp Ser, 50:239-240, 2006.

Multiple myeloma (MM) is a cancer of the plasma cells characterized by proliferation of malignant plasma cells and a subsequent overproduction of intact monoclonal immunoglobulin (IgG, IgA, IgD, or IgE) or Bence-Jones protein (free monoclonal κ and λ light chains). This incurable disease accounted for a disproportionate 2% cancer-related death rate in the United States in 2008 (Jemal A, et al. Cancer statistics, 2008. CA Cancer J Clin. 2008; 58:71-96). While current treatments including autologous transplantation (Harousseau J L, et al. Best Pract Res Clin Haematol. 2005; 18:603-618) have resulted in an improvement in overall survival (Kumar S K, et al. Blood. 2008; 111:2516-2520), there remains a need for delineating MM cell biology. It has been disclosed that overall proteasome activity of primary MM cells inversely correlates with apoptotic sensitivity to proteasome inhibition (Bianchi G et al. Blood, 26 2009, Vol. 113, No. 13, 3040-3049). The associated mechanism apparently involves triggering of stress responses which are characterized by an increase in the clearance of misfolded proteins by the 26S proteasome, an increase in the transcription and translation of chaperone proteins and foldases, and a strong decrease in global protein synthesis (Fribley A, et al. 2006. Cancer Biol Ther 5: 745-748; Bush K T, et al. J Biol Chem 272 (14) 1997 9086-9092.

Hepatic fibrosis is a common response to most chronic liver injuries, including viral hepatitis, parasitic infection, metabolic and immune diseases, congenital abnormalities, and drug and alcohol abuse. It is characterized by increased production of fibril-forming collagen and associated scar formation. Collagen is a family of proteins, wherein the constituent chains are generally about 300 amino acids in length, and are highly enriched in Gly-Pro and Pro-Gly repeating units. Currently, collagen is measured with DNA microarrays, which indicate the existence of collagen transcripts, but do not correlate well with actual synthesis of the protein.

In each of the above disease applications, it is important to rapidly and efficiently measure in real-time translation of a one or more particular proteins of interest. In some cases, it is important to study the subcellular localization of such proteins, as for example in the case of local protein synthesis in neurons.

FRET Technology

Fluorescence resonance energy transfer (FRET) is a method widely used to monitor biological interactions. FRET utilizes a donor fluorophore, having an emission spectrum that overlaps with the excitation spectrum of the acceptor fluorophore. Only when the donor fluorophore and acceptor fluorophore are in close proximity, typically about 10 nm, is a signal emitted from the acceptor fluorophore. FRET is described in Szöllosi J, Damjanovich S, Mátyus L, Application of fluorescence resonance energy transfer in the clinical laboratory: routine and research, Cytometry 34(4):159-79, 1998.

Existing Methods of Measuring Protein Translation

Cell assays that quantify production of a single specific protein typically require cell lysis and/or permeabilization, making then unsuitable for analysis of living cells. Further required are antibodies or other specific reagents directed to the protein of interest in conjunction with various dyes and detection reagents. Further, such methods produce an estimation of the total production of proteins over a given period of time measured in minute, hours or days. Those methods which are suitable for intact cells and organelles, such as metabolic labeling with radioactive tracers, are unable to isolate a signal from a particular transcript or protein of interest, and thus do not provide real-time or dynamic measurements of translation activity.

U.S. Pat. No. 6,210,941 to Rothschild discloses methods for the non-radioactive labeling, detection, quantitation and isolation of nascent proteins translated in a cellular or cell-free translation system. tRNA molecules are mis-aminoacylated with non-radioactive markers that may be non-native amino acids, amino acid analogs or derivatives, or substances recognized by the protein synthesizing machinery. U.S. Patent Application Publication Nos. 2003/0219783 and 2004/0023256 of Puglisi disclose compositions and methods for solid surface translation, where translationally competent ribosome complexes are immobilized on a solid surface. According to the disclosure, ribosomes and one or more components of the ribosome complex may be labeled to permit analysis of single molecules for determination of ribosomal conformational changes and translation kinetics.

WO 2004/050825 of one of the inventors of the present invention discloses methods for monitoring the synthesis of proteins by ribosomes in cells or a cell-free translation system, involving use of donor and acceptor fluorophores to label two locations of a ribosome, or each of a ribosome and a tRNA, or each of a ribosome and an amino acid.

WO 2005/116252 of one of the inventors of the present invention discloses methods for identifying ribonucleotide sequences of mRNA molecules using immobilized ribosomes in a cell-free translation system. In the disclosed methods, a tRNA and a ribosome component are engineered to carry donor and acceptor fluorophores or are used in FRET via their natural fluorescent properties.

The prior art does not disclose or suggest a method for measuring rates of translation of a protein of interest in living cells which utilizes a pair of tRNA molecules directly labeled with two components constituting a FRET pair, wherein the pair of tRNAs corresponds to a specific pair of adjacent amino acids occurring in the protein. There is an ongoing need for such methods. Methods for measuring changes in protein synthesis rates in response to a drug candidate would be very useful for drug screening and assays for predicting therapeutic activity of candidate drugs. Also highly advantageous would be methods for measuring translation of a protein of interest that are amenable for high-throughput screening and cell sorting.

SUMMARY OF THE INVENTION

The present invention provides systems and methods for measuring protein translation and methods for real time measurements of translation of a selected protein of interest in viable cells and subcellular compartments and organelles thereof.

The invention is based in part, on detection of an emitted FRET signal indicating translation of a predetermined codon pair within an mRNA sequence encoding a protein of interest. The FRET signal is produced by the juxtaposition of two tRNAs, i.e. a tRNA pair, within the ribosome complex during protein translation. The two tRNAs selected to form the tRNA pair must correspond to tRNAs which read the adjacent codons on the mRNA encoding the protein of interest. Each tRNA of the tRNA pair is labeled with a component of a FRET pair, namely either a FRET donor fluorophore or a FRET acceptor fluorophore.

As used herein, the term "tRNA pair" refers to a specific pair of tRNA species that are processed in consecutive order by a ribosome during translation of an mRNA sequence.

Each tRNA member of the tRNA pair is capable of "reading" one codon of the codon pair. Thus, the cognate amino acid of each tRNA of the tRNA pair corresponds to one amino acid encoded by a codon in the codon pair.

Without being bound by any theory or mechanism of action, the selection of the tRNA pair is an important determinant for carrying out the invention, since the signal emitted upon its translation must be representative of the mRNA encoding the specific protein of interest. Accordingly, in particular embodiments, the tRNA pair is preferably one which translates a codon pair which occurs at a relatively higher frequency in the mRNA encoding the protein, as compared to the occurrence of the same codon pair in other mRNAs being translated in the same cell, tissue or organism under examination. Consequently, in some preferred embodiments, the tRNA pair may be selected on the basis of the enrichment factor of the corresponding codon pair within the mRNA encoding the protein of interest.

The present invention advantageously provides readouts of the rate of synthesis of a selected protein of interest in a cell, including that localized to a subcellular compartment of the cell. The present invention can be carried out in any type of cell, including primary cells and cell lines, with relatively mild intervention in the cellular machinery and without requiring single ribosome analysis. The invention can be utilized for numerous applications, including, but not limited to, diagnostic assays, macroscopic assays, microscopic assays, high-throughput screening, cell enrichment and cell sorting, applications in biomanufacturing, and in numerous protein synthesis-related diseases. Measurements of rates of protein translation can be obtained in real time, which is crucial for instantly monitoring responses to various stimuli, particularly changes in environmental conditions, such as temperature, or exposure to specific compounds, such as small molecule drug candidates, biotherapeutic agents, or any other substances which potentially affect protein synthesis. The present invention is thus advantageous for studying the effects of drugs and drug candidates on cells in disease states characterized by aberrations in protein translation, and for studying rates of synthesis of target therapeutic proteins in stem cell and recombinant cell culture systems.

According to a first aspect, the present invention provides a system for measuring translation of a protein of interest, the system comprising a cell, wherein the cell comprises:

(i) a nucleic acid sequence encoding a protein of interest, wherein the nucleic acid sequence comprises at least one predetermined codon pair; and (ii) at least one tRNA pair, wherein for any one tRNA pair in the system, each tRNA member of the tRNA pair is capable of reading one codon of the at least one predetermined codon pair; and further wherein one tRNA member of each tRNA pair is labeled with a donor fluorophore and the other tRNA member of the tRNA pair is labeled with an acceptor fluorophore, and wherein the donor fluorophore and the acceptor fluorophore together form a FRET pair.

In a particular embodiment, each tRNA member of a tRNA pair is a single tRNA species. In a particular embodiment, the cognate amino acid of each tRNA member of a tRNA pair corresponds to one amino acid encoded by a predetermined codon pair. In a particular embodiment, the codon pair encodes a predetermined dipeptide occurring in the protein of interest. In a particular embodiment, the predetermined codon pair encodes amino acids occurring in adjacent positions in the protein of interest. In a particular embodiment, the amino acids occur in adjacent positions in the protein of interest in the order from C-terminus to N-terminus, or in the order from N-terminus to C-terminus.

In a particular embodiment, the system comprises a single tRNA pair. In a particular embodiment, the system comprises a plurality of tRNA pairs. In a particular embodiment, the plurality of tRNA pairs comprises the complete set of isoacceptor tRNAs specific for one amino acid encoded by a predetermined codon pair. In a particular embodiment, the plurality of tRNA pairs comprises a subset of isoacceptor tRNAs specific for one amino acid encoded by a predetermined codon pair.

In a particular embodiment, the plurality of tRNA pairs comprise tRNA species that have cognate amino acids that are different one from the other.

In a particular embodiment, the plurality of tRNA pairs is selected independently of their cognate amino acids.

In a particular embodiment, the plurality of tRNA pairs comprises a first complete set of isoacceptor tRNAs specific for a first amino acid encoded by a predetermined codon pair, and further comprises a second complete set of isoacceptor tRNAs specific for a second amino acid encoded by the same predetermined codon pair. In a particular embodiment, each of the isoacceptor tRNAs of the first complete set are labeled with the same donor fluorophore, and each of the isoacceptor tRNAs of the second complete set are labeled with the same acceptor fluorophore. In a particular embodiment, each of the isoacceptor tRNAs of the first complete set are labeled with the same acceptor fluorophore, and each of the isoacceptor tRNAs of the second complete set are labeled with the same donor fluorophore.

In particular embodiments, the first complete set is labeled with a plurality of different donor fluorophores. In particular embodiments, the first complete set is labeled with a plurality of different acceptor fluorophores. In particular embodiments, the second complete set is labeled with a plurality of different donor fluorophores. In particular embodiments, the second complete set is labeled with a plurality of different acceptor fluorophores.

In a particular embodiment, the plurality of tRNA pairs comprises a first subset of isoacceptor tRNAs specific for a first amino acid encoded by a predetermined codon pair, and further comprises a second subset of isoacceptor tRNAs specific for a second amino acid encoded by the same predetermined codon pair. In a particular embodiment, each of the isoacceptor tRNAs of the first subset are labeled with the same donor fluorophore, and each of the isoacceptor tRNAs of the second subset are labeled with the same acceptor fluorophore. In a particular embodiment, each of the isoacceptor tRNAs of the first subset are labeled with the same acceptor fluorophore, and each of the isoacceptor tRNAs of the second subset are labeled with the same donor fluorophore.

In a particular embodiment, the first subset is labeled with a plurality of different donor fluorophores. In particular embodiments, the first subset is labeled with a plurality of different acceptor fluorophores. In particular embodiments, the second subset is labeled with a plurality of different donor fluorophores. In particular embodiments, the second subset is labeled with a plurality of different acceptor fluorophores.

In a particular embodiment, the plurality of tRNA pairs comprises a complete set of isoacceptor tRNAs specific for a first amino acid encoded by a predetermined codon pair, and further comprises a subset of isoacceptor tRNAs specific for a second amino acid encoded by the same predetermined codon pair. In a particular embodiment, each of the isoacceptor tRNAs of the complete set are labeled with the same donor fluorophore, and each of the isoacceptor tRNAs of the subset are labeled with the same acceptor fluorophore. In a particular embodiment, each of the isoacceptor tRNAs of the complete set are labeled with the same acceptor fluorophore, and each of the isoacceptor tRNAs of the subset are labeled with the same donor fluorophore.

In a particular embodiment, the complete set is labeled with a plurality of different donor fluorophores and the subset is labeled with a plurality of different acceptor fluorophores. In a particular embodiment, the complete set is labeled with a plurality of different acceptor fluorophores and the subset is labeled with a plurality of different donor fluorophores.

Each possibility represents a separate embodiment of the present invention.

In a particular embodiment, the system comprises a plurality of isoacceptor tRNAs specific for one amino acid encoded by a predetermined codon pair. In a particular embodiment, each of the isoacceptor tRNAs specific for said one amino acid is labeled with the same donor fluorophore. In a particular embodiment, each of the isoacceptor tRNAs specific for said one amino acid is labeled with the same acceptor fluorophore. In a particular embodiment, the plurality of isoacceptor tRNAs specific for said one amino acid is labeled with a plurality of different acceptor fluorophores. In a particular embodiment, the plurality of isoacceptor tRNAs specific for said one amino acid is labeled with a plurality of different donor fluorophores.

Each possibility represents a separate embodiment of the present invention.

In a particular embodiment, the system comprises a first plurality of isoacceptor tRNAs specific for a first amino acid that is encoded by one codon of a predetermined codon pair, and further comprises a second plurality of isoacceptor tRNAs specific for a second amino acid that is encoded by the other codon of the same predetermined codon pair. In a particular embodiment, the first plurality is labeled with the same donor fluorophore, and the second plurality is labeled with the same acceptor fluorophore. In a particular embodiment, the first plurality is labeled with the same acceptor fluorophore, and the second plurality is labeled with the same donor fluorophore. In a particular embodiment, the first plurality of isoacceptor tRNAs is labeled with a plurality of different donor fluorophores and the second plurality of isoacceptor tRNAs is labeled with a plurality of different acceptor fluorophores. In a particular embodiment, the first plurality of isoacceptor tRNAs is labeled with a plurality of different acceptor fluorophores and the second plurality of isoacceptor tRNAs is labeled with a plurality of different donor fluorophores.

In a particular embodiment, one member of any one tRNA pair is capable of reading one codon of each of a plurality of predetermined codon pairs.

In a particular embodiment, one member of any one tRNA pair is capable of reading synonymous codons encoding a particular amino acid.

In particular embodiments, the cell is a live cell or a fixated cell. In particular embodiments, the cell is selected from the group consisting of human cells, non-human mammalian cells, vertebrate cells, avian cells, insect cells, yeast cells and plant cells.

In a particular embodiment, the system is for measuring translation of a protein within a subcellular compartment of a live cell. In a particular embodiment, the tRNA pair labeled with the FRET pair is localized to a subcellular compartment. In particular embodiments, the subcellular compartment is selected from the group consisting of dendritic spines, mitochondria, endoplasmic reticulum (ER) and chloroplasts.

In a particular embodiment, the nucleic acid sequence is an mRNA sequence.

In particular embodiments, the predetermined codon pair occurs at a frequency in the mRNA encoding the protein that is relatively higher, as compared to the frequency of the translation product of the same codon pair in the proteome of the cell or a subcellular compartment thereof. In particular embodiments, the frequency of said translation product in the proteome is that determined at a given time point.

In particular embodiments, the predetermined codon pair occurs at a frequency in the mRNA encoding the protein that is relatively higher, as compared to the frequency of the same codon pair in the transcriptome of the cell or a subcellular compartment thereof.

In particular embodiments, the nucleic acid sequence encoding the protein of interest has been altered to increase the frequency of a predetermined codon pair. In a particular embodiment, the nucleic acid sequence encoding the protein of interest has been altered to decrease the frequency of a predetermined codon pair.

In particular embodiments, the predetermined codon pair occurs in duplicate in adjacent positions in the mRNA encoding the protein of interest. In particular embodiments, opposite orientations of the predetermined codon pair occur in adjacent positions in the mRNA encoding the protein of interest. In a particular embodiment, at least one of the orientations of the predetermined codon pair occurs in the mRNA encoding the protein of interest at a frequency that is relatively higher, as compared to the frequency of the same codon pair in the transcriptome of the cell.

In a particular embodiment, the codons read by the tRNA pair together correspond to an adjacent codon pair, wherein the adjacent codon pair occurs within an mRNA transcript encoding the protein of interest at a frequency that is relatively higher, as compared to the frequency of the translation product of the same codon pair in the proteome of the cell or a subcellular compartment thereof. In a particular embodiment, the frequency of said translation product in the proteome is that determined at a given time point.

In a particular embodiment, the codons read by the tRNA pair together correspond to an adjacent codon pair, wherein the adjacent codon pair occurs within an mRNA transcript encoding the protein of interest at a frequency that is relatively higher, as compared to the same adjacent codon pair in the transcriptome of the cell or a subcellular compartment thereof.

In a particular embodiment, the system comprises two or more tRNA pairs labeled with two or more FRET pairs. In a particular embodiment, the system comprises two tRNA pairs, wherein each of the codon pairs translated by the respective tRNA pairs occurs at a frequency in the mRNA encoding the protein that is relatively higher, as compared to the frequency of the translation product of the same codon pairs in the proteome of the cell. In a particular embodiment, the frequency of said translation product in the proteome is that determined at a given time point.

In a particular embodiment, the system comprises two tRNA pairs, wherein each of the codon pairs translated by the respective tRNA pairs occurs at a frequency in the mRNA encoding the protein that is relatively higher, as compared to the frequency of the same codon pairs in the transcriptome of the cell.

In a particular embodiment, the system comprises two different tRNA pairs, wherein each tRNA pair corresponds to a distinct codon pair, and wherein each distinct codon pair occurs in one of two different mRNAs respectively encoding two different proteins of interest. In a particular embodiment, the system comprises two different tRNA pairs and two different mRNAs respectively encoding two different proteins of interest, wherein each tRNA pair corresponds to a distinct codon pair in one of the two different mRNAs.

In a particular embodiment, each codon pair occurs in its respective mRNA at a frequency that is relatively higher, as compared to the occurrence of the translation product of the same codon pair in the proteome of the cell. In a particular embodiment, the frequency of said translation product in the proteome is that determined at a given time point.

In a particular embodiment, one tRNA pair corresponds to a codon pair which occurs in its respective mRNA at a frequency that is relatively higher, as compared to the frequency of the translation product of the same codon pair in the proteome of the cell. In a particular embodiment, the frequency of said translation product in the proteome is that determined at a given time point.

In another embodiment, there is provided a system for sorting a cell population based on the expression level of a protein of interest in the cells. The cell sorting system comprises the system of the invention described herein, a means of measuring a detectable signal produced in a cell as a result of translation of the protein of interest, and a means of sorting the cells.

Further provided is a system for enriching a cell population having a particular level of expression of a protein of interest. The cell enriching system comprises the system of the invention described herein, a means of measuring a detectable signal produced in a cell as a result of translation of the protein of interest, and a means of sorting the cells so as to enrich for the population of cells having the desired expression level of the protein.

In another aspect, the present invention provides a method for measuring translation of a protein of interest in a biological sample comprising at least one cell, the method comprising the steps of:

(i) selecting a first codon pair which occurs in the mRNA sequence encoding a protein of interest at a known frequency;

(ii) introducing into the biological sample comprising cells at least one first tRNA pair, wherein for each first tRNA pair, each tRNA member of the pair is capable of reading one codon of the first codon pair selected in (i); and wherein one tRNA member of the tRNA pair is labeled with a donor fluorophore and the other tRNA member of the tRNA pair is labeled with an acceptor fluorophore, and wherein the donor fluorophore and the acceptor fluorophore together form a first FRET pair; and (iii) detecting FRET signals emitted from the biological sample during protein translation, thereby measuring translation of the protein of interest.

In particular embodiments, the codon pair selected in (i) occurs in the mRNA sequence at a frequency that is relatively higher, as compared to the frequency of the translation product of the same codon pair in the proteome of the cell, or a subcellular compartment thereof. In particular embodiments, the frequency of said translation product is that determined at a given time point.

Additional particular embodiments of the cell, the codon pair, the tRNA pair and the FRET pair are as hereinbefore described.

In a particular embodiment, the biological sample is selected from the group consisting of a cell line, a primary cell culture and a whole organism. In a particular embodiment, the step of introducing is into cells selected from the group consisting of human cells, non-human mammalian cells, vertebrate cells, avian cells, insect cells, yeast cells and plant cells. In a particular embodiment, the biological sample comprises diseased cells. In a particular embodiment, the step of introducing is into a subcellular compartment of living cells. In particular embodiments, the subcellular compartment is selected from the group consisting of dendritic spines, mitochondria, endoplasmic reticulum (ER) and chloroplasts.

In a particular embodiment, the whole organism is a model organism used for genetic research. In another embodiment, the model organism is selected from the group consisting of *Escherichia. coli, Caenorhabditis elegans, Drosophila melanogaster, Arabidopsis thaliana*, and an inbred strain of *Mus musculus*.

In a particular embodiment, the method further comprises a step of irradiating the biological sample with electromagnetic radiation prior to the step of detecting the emitted FRET signals, wherein the electromagnetic radiation used for irradiating is of a wavelength different from the detected FRET signals.

In a particular embodiment, the method further comprises a step of altering the nucleic acid sequence of the gene encoding the protein of interest so as to increase the frequency of the codon pair in the mRNA sequence encoding the protein.

In a particular embodiment, the method further comprises:

(iv) selecting a second codon pair, wherein the second codon pair occurs in the mRNA sequence encoding the protein of interest at a frequency that is relatively higher, as compared to the frequency of the translation product of the second codon pair in the proteome of the cell; and (v) introducing into the biological sample at least one second tRNA pair, wherein each tRNA member of the pair is capable of reading one codon of the second codon pair selected in (iv), wherein each tRNA member of the second tRNA pair is labeled with either a second donor fluorophore or a second acceptor fluorophore, and wherein the second donor fluorophore and the second acceptor fluorophore together form a second FRET pair.

In a particular embodiment of the method, each of the at least one first tRNA pair and the at least one second tRNA pair comprises a distinct plurality of tRNA pairs. The plurality of tRNA pairs relating to the first tRNA pair is referred to herein as "the first tRNA pair plurality"; and the plurality of tRNA pairs relating to the second tRNA pair is referred to herein as "the second tRNA pair plurality".

In a particular embodiment, the first tRNA pair plurality comprises the complete set of isoacceptor tRNAs specific for one amino acid encoded by the first codon pair or a subset of said isoacceptor tRNAs. Each possibility represents a different embodiment of the invention. In a particular embodiment, the first tRNA pair plurality comprises a complete set of isoacceptor tRNAs specific for each of the two amino acids encoded by the first codon pair.

In a particular embodiment, the second tRNA pair plurality comprises the complete set of isoacceptor tRNAs specific for one amino acid encoded by the second codon pair or a subset of said isoacceptor tRNAs. Each possibility represents a different embodiment of the invention. In a particular embodiment, the second tRNA pair plurality comprises a complete set of isoacceptor tRNAs specific for each of the two amino acids encoded by the second codon pair.

In a particular embodiment, each distinct plurality of tRNA pairs comprises tRNA species that have cognate amino acids that are different one from the other. In a particular embodiment, each of the isoacceptor tRNAs of the first tRNA pair plurality are labeled with the same donor fluorophore or with a plurality of different donor fluorophores. In a particular embodiment, each of the isoacceptor tRNAs of the second tRNA pair plurality are labeled with the same acceptor fluorophore or with a plurality of different acceptor fluorophores. In a particular embodiment, each of the isoacceptor tRNAs of the first tRNA pair plurality are labeled with the same acceptor fluorophore or with a plurality of different acceptor fluorophores. In a particular embodiment, each of the isoacceptor tRNAs of the second tRNA pair plurality are labeled with the same donor fluorophore or with a plurality of different donor fluorophores. Each possibility is a different embodiment of the invention.

In a particular embodiment, the system comprises distinct subsets of isoacceptor tRNAs specific for each amino acid encoded by the first codon pair and the second codon pair.

In a particular embodiment, each distinct subset of isoacceptor tRNAs is labeled with a single donor fluorophore or with a plurality of different donor fluorophores. In a particular embodiment, each distinct subset of isoacceptor tRNAs is labeled with a single acceptor fluorophore or with a plurality of different acceptor fluorophores. Each possibility is a different embodiment of the invention.

In a particular embodiment, the introducing of the second tRNA pair in (v) is into a cell or subcellular compartment that is other than that into which the first tRNA pair is introduced in (ii).

In a particular embodiment, the first codon pair occurs in the mRNA sequence of the protein of interest at a frequency that is relatively higher, as compared to the frequency of the translation product of the same codon pair in the proteome of a subcellular compartment of the cell, and the introducing of the first tRNA pair in (ii) is into the same subcellular compartment In a particular embodiment, at least one of the acceptor fluorophore and the donor fluorophore of the second FRET pair is other than that of the first FRET pair. In a particular embodiment, the acceptor fluorophore and the donor fluorophore of the second FRET pair are both other than that of the first FRET pair.

In a particular embodiment, the method further comprises altering a nucleic acid sequence of the gene encoding the protein so as to increase the frequency of the second codon pair in the mRNA sequence encoding the protein of interest.

In a particular embodiment, opposite orientations of the second codon pair occur in adjacent positions in the mRNA sequence encoding the protein of interest.

In one embodiment, the selecting in (i) is of a codon pair which occurs in the mRNA sequence of the protein of interest at a frequency that is relatively higher, as compared to the frequency of the translation of the same codon pair in the proteome of the cell, and the introducing of the tRNA pair in (ii) is into the cell.

In a particular embodiment, the subcellular compartment is an organelle. In another embodiment, the detected FRET signals are quantitated, thereby providing a readout in real-time of the amount of translation of the protein of interest.

In particular embodiments, the methods of the invention further comprise a step of analyzing the detected FRET signals, thereby obtaining a read-out of translation of the protein of interest. In particular embodiments, analysis of the signals produces a read-out of a parameter of translation activity of the protein of interest.

In particular embodiments, the methods further comprise a step of analyzing the detected FRET signals, thereby obtaining an estimate of the translation of the protein of interest. In particular embodiments, the step of analyzing comprises the step of computing the number of events (N) over a period of time t, wherein $$N \sim \frac{\sum I_t^2}{\sum \delta I_t^2}$$

wherein $I_t$ is the average signal strength at time t and $\delta I_t$ is the average signal deviation at time t. Each possibility represents a separate embodiment of the present invention.

In particular embodiments, there is provided a method for sorting a cell population based on the expression level of a protein, the method comprising performing a method described herein in intact cells and further comprising a step of sorting said cells so as to obtain a sorted cell population.

In particular embodiments, there is provided a method for enriching for a cell population based on the expression level of a protein, the method comprising performing a method described herein in intact cells and further comprising a step of sorting said cells so as to obtain a cell population enriched in the expression level of the protein.

According to some embodiments, the methods of the present invention further comprise a step of comparing the amount of detected FRET signals to a reference standard. In another embodiment, a level of detected FRET signals different from the reference standard is indicative of a disease or disorder. In another embodiment, the level of detected FRET signals is diagnostic for a disease, disorder or pathological condition. In another embodiment, the readout provided upon analysis of said detected FRET signals is diagnostic for a disease, disorder or pathological condition. Thus, methods of the present invention can be used to detect in a subject a condition selected from the group consisting of a disease, a disorder and a pathological condition.

According to one embodiment, the condition is selected from the group consisting of fragile X mental retardation, autism, aging and memory degeneration.

According to another embodiment, the disease is selected from the group consisting of a mitochondria-related disease, cardiac hypertrophy, restenosis, diabetes, obesity, a genetic disease resulting from a premature termination codon (PTC), and inflammatory bowel disease.

According to another embodiment, the pathological condition is a malignant or pre-malignant condition. In one embodiment, the malignant or pre-malignant condition is in a hematological cell. In one embodiment, the malignant condition is a hematological malignancy. In one embodiment, the hematological malignancy is selected from the group consisting of acute lymphoblastic leukemia (ALL); acute myelogenous leukemia (AML); chronic myelogenous leukemia (CML); Hodgkin's disease; non-Hodgkin lymphoma; chronic lymphocytic leukemia (CLL); diffuse large B-cell lymphoma (DLBCL); follicular lymphoma (FL); mantle cell lymphoma (MCL); hairy cell leukemia (HCL); marginal zone lymphoma (MZL); Burkitt's lymphoma (BL); post-transplant lymphoproliferative disorder (PTLD); T-cell prolymphocytic leukemia (T-PLL); B-cell prolymphocytic leukemia (B-PLL); Waldenstrom's macroglobulinemia and multiple myeloma (MM). In one embodiment, the malignant disorder is multiple myeloma.

In one embodiment, the pre-malignant condition is selected from the group consisting of monoclonal gammopathy of uncertain significance and smoldering multiple myeloma.

In other embodiments, a method of the present invention further comprises the step of administering to a cell or subcellular compartment at least one drug candidate prior to the step of detecting emitted FRET signals. According particular embodiments, the method is performed on separate biological samples, wherein the samples are substantially identical, except that one sample is analyzed following contact with the drug candidate, and the other sample has not been contacted with the drug candidate. "Substantially identical" as used herein refers to the absence of apparent differences between the biological samples. A non-limiting example of biological samples that are substantially identical is a set of two different aliquots from the same preparation of cells or subcellular organelles. Each possibility represents a separate embodiment of the present invention.

In other embodiments, the above method further comprises the step of comparing the intensities of FRET signals emitted from the two biological samples, i.e. those contacted and not contacted with the drug candidate. In other embodiments of this method, a difference between these two intensities, in particular a statistically significant difference, indicates that the drug candidate affects protein translation. Each possibility represents a separate embodiment of the present invention.

According to other embodiments, a method of the present invention further comprises the steps of (a) administering to the biological sample a drug candidate; (b) detecting the FRET signals emitted by the biological sample, as described herein; and (c) comparing the FRET signals detected in the presence of the drug candidate, to that detected in the absence of the drug candidate, thereby evaluating the effect of the drug candidate on protein translation.

According to a particular embodiment, a method for measuring the effect of a drug candidate on translation of a protein of interest comprises the steps of:
(i) introducing into a first biological sample a tRNA pair labeled with a FRET pair, wherein an acceptor fluorophore and a donor fluorophore together form the FRET pair and wherein each member of the tRNA pair is labeled with one of the acceptor fluorophore or the donor fluorophore, and wherein each member of the tRNA pair is capable of reading one codon of a predetermined codon pair, wherein the biological sample further comprises an mRNA transcript encoding the protein of interest, and wherein the predetermined codon pair occurs in the mRNA transcript;
(ii) providing a second biological sample that is substantially identical to the first biological sample;
(iii) introducing a drug candidate to one of the first biological sample and the second biological sample; and
(iv) measuring FRET signals emitted from each of the first and second biological samples, wherein a significant difference between the FRET signals measured in the first and second biological samples indicates that the drug candidate affects the translation of the protein of interest.

In other embodiments, methods and systems of the present invention are used for high-throughput-screening (HTS) of putative translation modulators.

According to a particular embodiment, the codon pair appears in the mRNA sequence encoding the protein of interest at a frequency that is higher, as compared to the frequency of—the translation product of the same codon pair in the proteome of the cell or a subcellular compartment thereof. According to a particular embodiment, the codon pair occurs in the mRNA sequence encoding the protein of interest at a frequency that is higher, as compared to the frequency of the same codon pair in the transcriptome of the cell or a subcellular compartment thereof.

According to particular embodiments, the drug candidate of the present invention is selected from the group consisting of a small molecule, a peptide, an enzyme, a hormone, and a biotherapeutic agent.

According to another aspect, there is provided a method for measuring the effect of a drug candidate on translation of a protein of interest in a biological sample, said method comprising the steps of:
(i) selecting a specific codon pair which occurs in the mRNA sequence encoding a protein of interest at a frequency that is relatively higher, as compared to the frequency—of the translation product of the same codon pair in the proteome of the biological sample;
(ii) introducing into the biological sample a tRNA pair labeled with a FRET pair, wherein an acceptor fluorophore and a donor fluorophore together form the FRET pair and wherein each member of the tRNA pair is labeled with one of the acceptor fluorophore or the donor fluorophore, and wherein each member of the tRNA pair is capable of reading one codon of a codon pair appearing in the mRNA sequence encoding the protein of interest, and wherein the biological sample further comprises a nucleic acid sequence encoding said protein of interest;
(iii) measuring FRET signals emitted from the biological sample;
(iv) contacting the biological sample with a drug candidate; and
(v) measuring FRET signals emitted from said acceptor fluorophore, under the conditions of (iv), wherein a difference between the FRET signals measured in step (iii) and the FRET signals measured in step (v) indicates that said drug candidate affects translation of the protein of interest.

In a particular embodiment, the biological sample is selected from the group consisting of a cell and a subcellular compartment thereof.

According to other embodiments of the methods and systems of the present invention, the protein of interest is selected from the group consisting of insulin, a growth factor, an antibody, erythropoietin, and a stem cell specialization factor.

According to some embodiments, the protein of interest further comprises a protein tag. According to other embodiments, the protein of interest is a fusion protein comprising a protein tag. According to other embodiments, the protein tag is selected from the group consisting of an affinity tag, a solubilization tag, a chromatography tag, an epitope tag and a fluorescent protein tag. According to some embodiments, the translation product of the tRNA pair occurs in the protein tag.

These and other embodiments of the present invention will become apparent in conjunction with the figures, description and claims that follow.

BRIEF DESCRIPTION OF THE FIGURES

The invention is herein described, by way of example only, with reference to the accompanying figures. With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the figures making apparent to those skilled in the art how the several forms of the invention may be embodied in practice.

FIG. 6 shows real-time single molecule fluorescence traces of a single ribosome translating a known mRNA.

DETAILED DESCRIPTION OF THE INVENTION

Definitions

Figure 1:
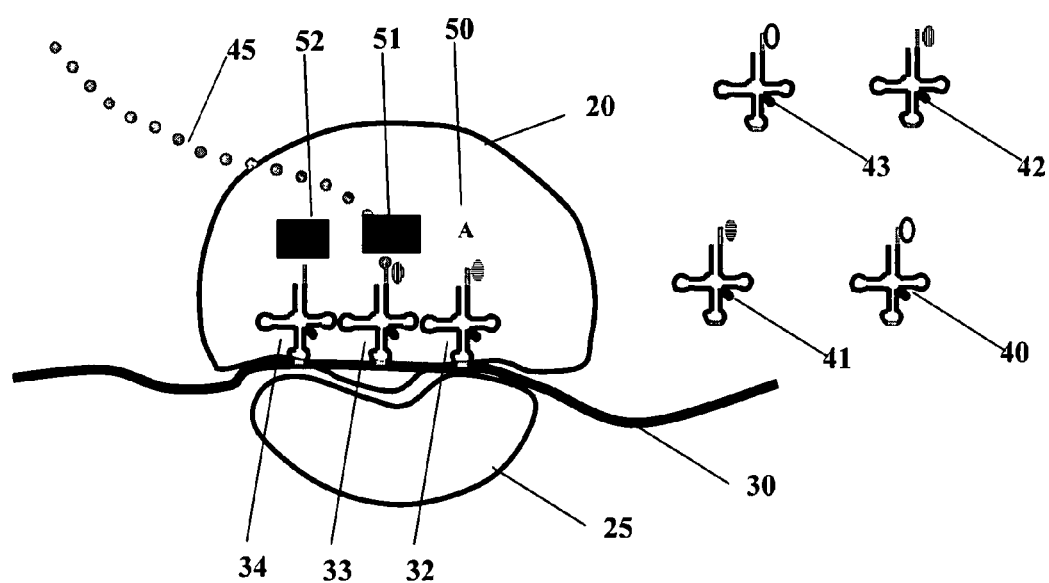
FIG. 1 is a schematic presentation of a bacterial ribosome structure with the large (50S) subunit 20, small (30S) subunit 25, aminoacyl (A) site 50 where the tRNAs are initially docked, peptidyl (P) site 51 where the growing polypeptide chain is docked, and exit (E) site 52 wherefrom the deacylated tRNA is removed once the cycle is complete. On the right side, tRNAs that are still undocked, i.e. 40, 41, 42 and 43, are depicted. mRNA being decoded 30 and the nascent polypeptide chain being synthesized 45 are also depicted. The ribosome itself is made up of large folded rRNA chains with ribosomal proteins. The large subunit 20 contains two folded rRNAs, known as 23S and 5S. The small subunit 25 contains one folded rRNA, 30S (not shown). On the folded rRNA chains more than 50 ribosomal proteins are docked (not shown). They are customarily denoted by L1, L2 etc. for the approximately 36 ribosomal proteins attached to the large subunit, and by S1, S2 etc. for the approximately 21 ribosomal proteins attached to the small subunit (numbers given are for E. coli ribosomes).

As used herein, the term "tRNA" refers to transfer ribonucleic acid. Specific tRNAs recognize specific codons in mRNA, generally involving standard base pairing between the mRNA codon and the tRNA anticodon, and in some cases involving wobble pairing between codon and anticodon. An "initiator tRNA" is a specific tRNA molecule that is used only for the initial amino acid of a synthesized polypeptide. A "suppressor tRNA" is a tRNA molecule that comprises an anticodon which allows pairing with a termination codon (e.g. UAG and UAA). An "elongator tRNA" is a tRNA molecule that is neither an initiator nor a suppressor, and that places its corresponding amino acid (i.e. cognate amino acid) in its proper sequence during the process of translation.

The terms "cognate amino acid" and "aminoacylating amino acid" are used herein interchangeably to refer to the specific amino acid that is carried by a particular elongator tRNA.

A tRNA is referred to as "charged" or "aminoacylated" when it is covalently associated with its cognate amino acid at the 3' terminal CCA end.

In most species, multiple tRNA molecules exist which are capable of being aminoacylated with the same amino acid, but have different anticodon sequences. Such families of tRNAs are termed "isoacceptor families". There are 21 isoacceptor families, corresponding to 20 for the standard amino acids and one for seleno-cysteine. In humans, 49 specific tRNA molecules exist (including that carrying seleno-cysteine), wherein 1 to 5 different tRNA molecules may be charged with a specific amino acid.

As used herein, the terms "isoaccepting tRNAs" and "isoacceptors" may encompass either the entire set of isoacceptors in an isoacceptor family, or a partial set i.e. subset, of isoacceptors in an isoacceptor family.

Reference herein to a tRNA specific for a particular amino acid may encompass all of the isoaccepting tRNAs for that amino acid, a subset of such isoacceptors, or a single tRNA capable of being aminoacylated by that amino acid, unless the context expressly specifies a single tRNA.

A particular tRNA may be denoted herein according to its aminoacylating amino acid, which is indicated in superscript such as in tRNA$^{Leu}$. A particular tRNA may additionally be denoted according to its anticodon, indicated in parentheses, such as tRNA$^{Leu}$ (CAG).

A particular tRNA may further be denoted herein in abbreviated form as Xi, wherein X is the single letter identification of its cognate amino acid and i is a numerical identifier (1≤i≤5) pertaining to the anticodon of the specific tRNA molecule and the codon(s) read by that tRNA molecule. Table 1 herein lists Xi identifiers for tRNAs of _Homo sapiens_.

TABLE 1

Characteristics of the tRNAs occurring in _Homo sapiens_ (excluding that specific for seleno-cysteine)

| No. | tRNA identifier | anticodon | codon1 read | codon2 (wobble) read |
|---|---|---|---|---|
| 1. | $A_1$ | AGC | GCT | GCC |
| 2. | $A_2$ | CGC | GCG | |
| 3. | $A_3$ | TGC | GCA | |
| 4. | $G_1$ | GCC | GGC | GGT |
| 5. | $G_2$ | CCC | GGG | |
| 6. | $G_3$ | TCC | GGA | |
| 7. | $P_1$ | AGG | CCT | CCC |
| 8. | $P_2$ | CGG | CCG | |
| 9. | $P_3$ | TGG | CCA | |
| 10. | $T_1$ | AGT | ACT | ACC |
| 11. | $T_2$ | CGT | ACG | |
| 12. | $T_3$ | TGT | ACA | |
| 13. | $V_1$ | AAC | GTT | GTC |
| 14. | $V_2$ | CAC | GTG | |
| 15. | $V_3$ | TAC | GTA | |
| 16. | $S_1$ | AGA | TCT | TCC |
| 17. | $S_2$ | CGA | TCG | |
| 18. | $S_3$ | TGA | TCA | |
| 19. | $S_4$ | GCT | AGC | AGT |
| 20. | $R_1$ | ACG | CGT | CGC |
| 21. | $R_2$ | CCG | CGG | |
| 22. | $R_3$ | TCG | CGA | |
| 23. | $R_4$ | CCT | AGG | |
| 24. | $R_5$ | TCT | AGA | |
| 25. | $L_1$ | AAG | CTT | CTC |
| 26. | $L_2$ | CAG | CTG | |
| 27. | $L_3$ | TAG | CTA | |
| 28. | $L_4$ | CAA | TTG | |
| 29. | $L_5$ | TAA | TTA | |

TABLE 1-continued

Characteristics of the tRNAs occurring in _Homo sapiens_ (excluding that specific for seleno-cysteine)

| No. | tRNA identifier | anticodon | codon1 read | codon2 (wobble) read |
|---|---|---|---|---|
| 30. | $F_1$ | GAA | TTC | TTT |
| 31. | $N_1$ | ATT | AAT | |
| 32. | $N_2$ | GTT | AAT | AAC |
| 33. | $K_1$ | CTT | AAG | |
| 34. | $K_2$ | TTT | AAA | |
| 35. | $D_1$ | GTC | GAC | GAT |
| 36. | $E_1$ | CTC | GAG | |
| 37. | $E_2$ | TTC | GAA | |
| 38. | $H_1$ | GTG | CAC | CAT |
| 39. | $Q_1$ | CTG | CAG | |
| 40. | $Q_2$ | TTG | CAA | |
| 41. | $I_1$ | AAT | ATT | |
| 42. | $I_2$ | GAT | ATC | |
| 43. | $I_3$ | TAT | ATA | |
| 44. | $M_1$ | CAT | ATG | |
| 45. | $Y_1$ | ATA | TAT | |
| 46. | $Y_2$ | GTA | TAC | TAT |
| 47. | $C_1$ | GCA | TGC | TGT |
| 48. | $W_1$ | CCA | TGG | |

The terms "reading" and "decoding" are used herein interchangeably to refer to the process in which a tRNA recognizes a particular codon on an mRNA during its translation on a ribosomal complex.

The term "synonymous codons" is used herein to refer to distinct codons that encode the same amino acid. Synonymous codons which differ only at the third base, may often be read by the same tRNA due to "wobble" pairing i.e., base pairing between a codon and an anticodon that does not obey the standard Watson-Crick pairing at the wobble position.

The term "tRNA pair" as used herein refers to a specific pair of tRNAs that are processed in consecutive order by a ribosome, as it synthesizes a protein by translating an mRNA molecule. Thus, for example, the two tRNA members of a tRNA pair will be held at the A and P sites of the ribosomal complex at a substantially close or identical time point during the process of translation.

The term "tRNA sequence" as used herein refers to a sequence of tRNAs used for translation of a particular mRNA molecule during synthesis of a particular protein, wherein the members of the sequence are processed in a consecutive manner by a ribosomal complex. A tRNA sequence may be denoted herein by a sequence of Xi identifiers, for example those indicated in Table 1, according to the order of the tRNAs used for the processing of the particular mRNA.

The terms "adjacent codon pair" and "codon pair" are used herein interchangeably to two distinct codons that appear in consecutive order in a nucleic acid sequence, such as an mRNA, either in the direction from 5' to 3', or in the direction from 3' to 5'.

The term "frequency" in reference to a codon or codon pair, refers to the number of occurrences of the codon or codon pair within a particular nucleic acid sequence, such as a specific mRNA sequence, or within a set of nucleic acid sequences, expressed as a percentage of the total number of codons or codon pairs occurring in the same nucleic acid sequence or set of nucleic acid sequences.

The term "enriched" in reference to a codon pair, means that the adjacent occurrence of the codons constituting the pair within a particular nucleic acid sequence, such as a specific mRNA sequence, is at higher frequency compared to the occurrence of the same codon pair in a reference nucleic acid sequence or set of nucleic acid sequences.

The term "enriched" in reference to a tRNA pair, means that the tRNA pair appears at higher frequency in the tRNA sequence of a particular protein, as compared to the occurrence of the same tRNA pair in a reference tRNA sequence or a set of tRNA sequences.

As used herein, the term "FRET" ("fluorescence resonance energy transfer"; also known as "Förster resonance energy transfer") refers to a physical phenomenon involving a donor fluorophore and a matching acceptor fluorophore selected so that the emission spectrum of the donor overlaps the excitation spectrum of the acceptor, and further selected so that when donor and acceptor are in close proximity (usually less than 10 nm), excitation of the donor will cause excitation of and emission from the acceptor, as some of the energy passes from donor to acceptor via a quantum coupling effect. Thus, a FRET signal serves as a proximity gauge of the donor and acceptor; only when they are in close proximity is a signal generated. The donor fluorophore and acceptor fluorophore are collectively referred to herein as a "FRET pair".

The terms "mRNA", "transcript" and "mRNA transcript" are used interchangeably herein to describe a ribonucleotide sequence that transfers genetic information to ribosomes, where it serves as a template for peptide or protein synthesis. Ribonucleotide sequences are polymers of ribonucleic acids, and are constituents of all living cells and many viruses. They consist of a long, usually single-stranded chain of alternating phosphate and ribose units with the bases adenine, guanine, cytosine, and uracil bonded to the ribose. The structure and base sequence of RNA are determinants of protein synthesis and the transmission of genetic information. In general, a "transcript" refers to a specific mRNA encoding a peptide or protein of interest.

As used herein, the terms "codon" and "triplet codon" refer interchangeably to the tri-nucleotide unit of a nucleic acid, such as mRNA, that encodes i.e. specifies a single amino acid. A nucleic acid sequence that encodes a specific peptide or protein is composed of a string of codons specifying the amino acid sequence of the protein. There are $4^3=64$ different codon combinations possible with a triplet codon of three nucleotides; all 64 codons are assigned for either amino acids or stop signals during translation.

As used herein, the terms "protein" and "polypeptide" refer interchangeably to a complex polymer compound composed of one or more linear chains of amino acids, wherein the amino acids are covalently joined together by peptide bonds between the carboxyl and amino groups of adjacent amino acid residues. The sequence of amino acids in a protein is determined by the corresponding nucleic acid sequence of the gene encoding the protein. Proteins include glycoproteins, antibodies, non-enzyme proteins, enzymes, hormones and peptides.

As used herein, the term "peptide" refers to a small to intermediate molecular weight chain of amino acids covalently joined by peptide bonds between adjacent amino acid residues. Peptides generally have from 2 to 100 amino acid residues and frequently but not necessarily represent a fragment of a larger protein. Peptides may be the products of native genes, produced either naturally, by recombinant techniques or chemical synthesis. Alternately, peptides may be non-naturally occurring sequences.

As used herein, "one member of the tRNA pair" refers to an individual tRNA species of a tRNA pair. The members of the tRNA pair may be the same or different tRNA species, but will be differentially labeled with acceptor fluorophore or donor fluorophore of a FRET pair.

As used herein, "cell" refers to a prokaryotic or a eukaryotic cell. Suitable cells can be, for example, of mammalian, avian, insect, bacterial, yeast or plant origin. Non-limiting examples of mammalian cells include human, bovine, ovine, porcine, murine, and rabbit cells. In another embodiment, the cell can be an embryonic cell, bone marrow stem cell, or other progenitor cell. In another embodiment, the cell is a somatic cell, which can be, for example, an epithelial cell, fibroblast, smooth muscle cell, blood cell (including a hematopoietic cell, red blood cell, T-cell, B-cell, etc.), tumor cell, cardiac muscle cell, macrophage, dendritic cell, neuronal cell (e.g., a glial cell or astrocyte), or pathogen-infected cell (e.g., those infected by bacteria, viruses, virusoids, parasites, or prions).

The term "test cell" as used herein, refers to cells that are manipulated for use in the translation assay of the invention.

The term "host cell" as used herein refers to cells that do not naturally contain the labeled elements of the invention.

As used herein, the term "biological sample" refers to any of: an organism, an organ, a tissue, a cell, a subcellular compartment or an organelle; or a portion, fragment or aliquot thereof, which is used in the methods and assays of the invention.

As used herein, the term "subcellular compartment" refers to any defined part of the cell where protein translation activity takes place, such as dendritic spines, mitochondria, endoplasmic reticulum (ER) and chloroplasts.

As used herein, the term "organelle" refers to cellular membrane-encapsulated structures such as the chloroplast, endoplasmic reticulum (ER) and mitochondrion.

As used herein, "introducing" refers to the transfer of molecules such as ribosomes, tRNAs, translation factors and amino acids from outside a host cell or subcellular compartment to inside a host cell or subcellular compartment. Said molecules can be "introduced" into a host cell or subcellular compartment by any means known to those of skill in the art, for example as taught by Sambrook et al. Molecular Cloning: A Laboratory Manual, Cold Spring Harbor Laboratory Press, New York (2001). Means of "introducing" molecules into a host cell or subcellular compartment include, but are not limited to heat shock, calcium phosphate transfection, electroporation, lipofection, and viral-mediated transfer.

The terms "polynucleotide", "nucleic acid" and "nucleic acid sequence" refer interchangeably to a polymeric form of nucleotides at least 10 bases in length. A polynucleotide may be present either in its genomic form or as an isolated polynucleotide. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (eg., a cDNA) independent of other sequences. The nucleotides of the invention can be ribonucleotides, deoxyribonucleotides, or modified forms of either nucleotide. The term includes single and double stranded forms of DNA.

As used herein, the term "transfection" refers to introduction of a nucleic acid sequence into the interior of a membrane-enclosed space of a living cell, including introduction of the nucleic acid sequence into the cytosol of a cell as well as the interior space of a mitochondria, endoplasmic reticulum (ER) or chloroplast. The nucleic acid may be in the form of naked DNA, RNA, or tRNA. The DNA, RNA, or tRNA is in some embodiments associated with one or more proteins. In another embodiment, the nucleic acid is incorporated into a vector. Each possibility represents a separate embodiment of the present invention.

As used herein, the term "infection" means the introduction of a nucleic acid such as DNA, RNA, tRNA into a recipient cell, subcellular compartment, or organism, by means of a virus. Viral infection of a host cell is a technique that is well established in the art and is described in a number of laboratory texts and manuals such as Sambrook et al., Molecular Cloning: A Laboratory Manual, Vol. 1-3, Cold Spring Harbor Laboratory, Cold Spring Harbor, N.Y., 2001.

As used herein, the terms "label", "detectable label" and "tag" refer interchangeably to a molecule that is attached to or associated with another molecule and that can be directly (i.e., a primary label) or indirectly (i.e., a secondary label) detected. For example, a label can be visualized and/or measured and/or otherwise identified so that its presence, absence, or a parameter or characteristic thereof can be measured and/or determined.

As used herein, the term "fluorescent label" refers to any molecule that can be detected via its inherent fluorescent properties, which include fluorescence detectable upon excitation. Suitable fluorescent labels include, but are not limited to, fluorescein, rhodamine, tetramethylrhodamine, eosin, erythrosin, coumarin, methyl-coumarins, pyrene, malachite green, stilbene derivatives, Lucifer yellow, Cascade Blue, Texas Red, IAEDANS, EDANS, boron-dipyrromethene (BODIPY), LC Red 640, LC Red 705, cyanine dyes such as Cy3, Cy 5 and Cy 5.5, and Oregon green, as well as to fluorescent derivatives thereof. Suitable optical dyes are described in The Handbook: A Guide to Fluorescent Probes and Labeling Technologies. 2005, Haugland, R P. 10$^{th}$ ed. Invitrogen/Molecular Probes; Carlsbad, Calif. Additional labels include but are not limited to fluorescent proteins, such as green fluorescent protein (GFP), yellow fluorescent protein (YFP), blue fluorescent protein (BFP), cyan fluorescent protein (CFP) etc.

As used herein, a "protein tag" refers to a peptide sequence that is genetically fused to a recombinant protein of interest. In general, protein tags are removable, for example by chemical agents or by enzymatic means. Protein tags may be used for facilitating purification and/or proper folding of a recombinant protein of interest. Protein tags are frequently referred to or classified according to their usage. Thus for example, affinity tags are protein tags that enable purification of the recombinant protein to which they are fused using an affinity technique. Examples of affinity tags include, without limitation, chitin binding protein (CBP), maltose binding protein (MBP), poly(His) and glutathione-S-transferase (GST). Solubilization tags assist in the proper folding in proteins and prevent their precipitation, such as for example, thioredoxin (TRX) and poly(NANP). Chromatography tags alter chromatographic properties of the protein to afford different resolution across a particular separation technique, such as for example, polyanionic amino acids, such as FLAG-tag. Epitope tags are short peptide sequences which are capable of eliciting production of high-affinity antibodies in many different species. Epitope tags include, without limitation, V5-tag, c-myc-tag, and HA-tag, and can be used in antibody or antigen purification. Further, a protein tag may be a fluorescent protein, such as those described above.

The term "affinity tag" as used herein refers to any amino acid sequence fused to a protein of interest at either the amino terminal or carboxy terminal end of the protein. Typically, the affinity tag is used for isolation and or detection purposes. The "affinity tag" may optionally be in the middle of the protein of interest such that when the corresponding nucleic acid sequence is translated the affinity tag is fused in frame into the protein of interest. The amino acid residues form a peptide that has affinity for a chemical moiety, a metal ion or a protein. The affinity tag may have an overall positive, negative or neutral charge; typically the affinity tag has an overall positive or negative charge.

The term "fusion protein" as used herein refers to a protein hybrid comprising amino acid sequence encoded by mRNA sequences from heterologous proteins, such as for example a therapeutic protein and a protein tag.

As used herein, the term "test compound" refers to a compound to be tested by one or more screening assays of the invention as a putative agent that modulates translation activity. The test compounds of the invention encompass numerous classes of chemical molecules, though typically they are organic molecules, and preferentially of low molecular weight. A drug candidate may be one type of test compound.

The term "modulator" as used herein is generic for an inhibitor or activator of translation.

As used herein, the term "transcriptome" refers to the total set of all messenger RNA (mRNA) molecules, or "transcripts", produced in one or a population of cells, or within a particular subcellular compartment, tissue or organism. The transcriptome reflects the genes that are being actively transcribed into mRNA at any given time, with the exception of mRNA species that are degraded due to phenomena such as transcriptional attenuation.

As used herein, the term "proteome" refers to the entire complement of translated proteins expressed by a cell, population of cells, subcellular compartment, tissue or organism. The proteome frequently does not reflect the transcriptome of the corresponding cell, subcellular compartment, etc, since substantial regulation occurs during translation, resulting in low correlation between a particular set of mRNA transcripts existing at a particular time point and the set of proteins that are actually translated from such available transcripts. The proteome is known to be dynamic and can change over time and/or in response to environmental conditions or exogenously added agents.

"Biotherapeutic agent," as used herein, refers to a protein, enzyme, metabolite, nucleic acid, or microorganism that has therapeutic characteristics. Biotherapeutic agents originate from nature but can be engineered to produce optimal therapeutic value. The term includes synthetic mimics of naturally occurring proteins, enzymes, metabolites, nucleic acids, and microorganisms. Each possibility represents a separate embodiment of the present invention.

The present invention provides systems for measuring and monitoring protein translation of specified proteins in viable cells and in specific subcellular compartments. The methods of the present invention are capable of providing a signal indicating the rate of synthesis of a particular protein of interest. The translation system of the present invention can be used to identify translation modulators in high-throughput screening (HTS).

The invention provides a system for measuring translation of a protein of interest in a cell. The system comprises a cell, wherein the cell comprises (i) a nucleic acid sequence encoding the protein of interest, and the nucleic acid is known to contain at least one predetermined codon pair or a codon pair of interest. The cell further comprises (ii) at least one tRNA pair labeled with a FRET pair. For any one tRNA pair in the system, each member of the tRNA pair is capable of reading one codon of a predetermined codon pair in the nucleic acid. Further, tRNA species corresponding to those of the labeled tRNA pair occur in consecutive order in the tRNA sequence of the protein of interest.

The codon pair may be selected on the basis of its encoding a dipeptide of interest. The predetermined codon pair may encode amino acids known to occur in adjacent positions in the protein of interest. Reference herein to amino acids occurring in adjacent positions means that their consecutive occurrence in the protein of interest may be in the order from C-terminus to N-terminus, or in the order from N-terminus to C-terminus.

Opposite orientations of the dipeptide may occur in adjacent positions in the amino acid sequence of the protein of interest. For example, the dipeptide arginine-phenylalanine (RF) may occur in opposite orientations as RFFR. In a particular embodiment, at least one of the opposite orientations of the dipeptide occurs in the amino acid sequence of the protein of interest at a frequency higher than its frequency in the proteome of the cell or subcellular compartment under study. In a particular embodiment, opposite orientations of the dipeptide occur in overlapping positions in the amino acid sequence of the protein of interest. For example, the dipeptide arginine-phenylalanine (RF) may occur as RFR.

In a particular embodiment, opposite orientations of the dipeptide occur in overlapping positions in the tRNA sequence of the protein of interest. In a particular embodiment, the codons recognized by the tRNA pair together correspond to an adjacent codon pair which occurs at a known frequency within an mRNA transcript encoding the protein of interest. For example, the adjacent codon pair may be known to occur within the mRNA transcript at a frequency that is higher than the frequency of the same codon pair in the transcriptome of the cell or subcellular compartment.

The predetermined codon pair may be selected on the basis of its frequency i.e. relative occurrence, within the mRNA encoding the protein. For example, in some preferred embodiments, the codon pair occurs at a frequency within the mRNA that is relatively higher, as compared to the frequency of the translation product of the same codon pair in the proteome of the cell, subcellular compartment, tissue or organism under examination. Further, the frequency at which the codon pair occurs within the mRNA may be compared to the frequency of its translation product in the proteome of the same system, at a given time point.

In other particular embodiments, the frequency of the predetermined codon pair in the mRNA may be compared to the frequency of the same codon pair in the transcriptome of the cell, subcellular compartment thereof, tissue or organism under examination.

In some embodiments, it may be advantageous to conduct the comparison of the frequency of a codon pair relative to that of the proteome, rather than the transcriptome of the biological system under examination. It is well documented that translational efficiency differs considerably for various eukaryotic mRNAs, thus leading to a significant statistical disparity between mRNA pools and the corresponding pool of protein products. For example, structural features of mRNAs which have been disclosed to influence their translational efficiency include the length of 5' UTRs, and G+C content of 5' UTRs (Kochetov et al., FEBS LEtt. 1998 Dec. 4; 440(3):351-5). It has further been disclosed that upstream ORFs in mRNAs have a significant impact on translation of human mRNAs with modest impact on mRNA levels (Calvo et al., Proc Natl Acad Sci U.S.A. 2009 May 5; 106(18)7507-12).

In addition, the system of the invention may comprise a cell in which a nucleic acid sequence of interest has been altered to increase the frequency of a predetermined codon pair. In some cases, the nucleic acid sequence may be altered to decrease the frequency of a predetermined codon pair.

As used herein, the term "altered" refers to the process of changing a nucleic acid sequence, for example, by site specific mutation so as to produce a nucleic acid different from the wild type nucleic acid. Methods for gene alteration are well known in the art, as disclosed $3^{rd}$ ed. for example in Sambrook et al (2000) "Molecular Cloning: A Laboratory Manual", Cold Spring Harbor Laboratory Press.

In particular embodiments, opposite orientations of a predetermined codon pair occur in adjacent positions in the mRNA encoding the protein of interest. For example, the codon pair CGT TTC, respectively encoding arginine-phenylalanine (RF), may appear in the mRNA sequence as CGT TTC TTC CGT. In a particular embodiment, at least one of the orientations of the predetermined codon pair occurs in the mRNA encoding the protein of interest at a frequency that is relatively higher, as compared to the frequency of the same codon pair in the transcriptome of the cell.

The invention further involves use of at least one labeled tRNA pair. Each tRNA pair includes two tRNA members, of which each member may correspond to a single tRNA species. The relationship between the tRNA pair and the predetermined codon pair is that the cognate amino acid of each tRNA member of the tRNA pair corresponds to one amino acid encoded by the predetermined codon pair.

Each member of the tRNA pair may be capable of reading the most frequently used codon on an mRNA molecule that encodes the cognate amino acid of the tRNA pair member. In a particular embodiment, at least one member of the tRNA pair is capable of reading the most frequently used codon on an mRNA molecule that encodes the cognate amino acid of the tRNA pair member.

The system may comprise a single tRNA pair, or a plurality of tRNA pairs. In particular embodiments, the plurality of tRNA pairs comprises the complete set of isoacceptor tRNAs specific for one amino acid encoded by a predetermined codon pair. In other cases, the plurality of tRNA pairs comprises a subset of isoacceptor tRNAs specific for one amino acid encoded by a predetermined codon pair.

The plurality of tRNA pairs may comprise tRNA species that have cognate amino acids that are different one from the other. However, a single tRNA pair or a plurality of tRNA pairs may be selected independently of their cognate amino acids.

In a particular embodiment, the plurality of tRNA pairs comprises a first complete set of isoacceptor tRNAs specific for a first amino acid encoded by a predetermined codon pair, and further comprises a second complete set of isoacceptor tRNAs specific for a second amino acid encoded by the same predetermined codon pair. In particular embodiments, each of the isoacceptor tRNAs of the first complete set may be labeled with the same donor fluorophore, in which case each of the isoacceptor tRNAs of the second complete set is labeled with the same acceptor fluorophore. Alternately, each of the isoacceptor tRNAs of the first complete set may be labeled with the same acceptor fluorophore, in which case each of the isoacceptor tRNAs of the second complete set is labeled with the same donor fluorophore.

However, in other embodiments, the first complete set of isoacceptors may be labeled with a plurality of different donor fluorophores, or with a plurality of different acceptor fluorophores, and similarly, in other embodiments, the second complete set may be labeled with a plurality of different acceptor fluorophores, or with a plurality of different donor fluorophores. As is readily understood by one of skill in the art, the labeling of the tRNAs is such that one set contains donor fluorophores and the other set contains acceptor fluorophores, so that FRET signals may be produced when the appropriately labeled tRNA pairs are localized in proximity within the same ribosomal complex.

In other embodiments, the plurality of tRNA pairs comprises a first subset of isoacceptor tRNAs specific for a first amino acid encoded by the predetermined codon pair, and further comprises a second subset of isoacceptor tRNAs specific for a second amino acid encoded by the same predetermined codon pair. Accordingly, each of the isoacceptor tRNAs of the first subset may be labeled with the same donor fluorophore, in which case each of the isoacceptor tRNAs of the second subset is labeled with the same acceptor fluorophore. Alternately, each of the isoacceptor tRNAs of the first subset may labeled with the same acceptor fluorophore, in which case each of the isoacceptor tRNAs of the second subset are labeled with the same donor fluorophore.

However, in other embodiments, the first subset may be labeled with a plurality of different donor fluorophores, or with a plurality of different acceptor fluorophores. Similarly, the second subset may be labeled with a plurality of different donor fluorophores, or with a plurality of different acceptor fluorophores.

As is readily understood by one of skill in the art, the labeling of the tRNAs is such that one of the subsets contains donor fluorophores and the other subset contains acceptor fluorophores, so that FRET signals may be produced when the appropriately labeled tRNA pairs are localized in proximity within the same ribosomal complex.

In particular embodiments, the plurality of tRNA pairs comprises a complete set of isoacceptor tRNAs specific for a first amino acid encoded by a predetermined codon pair, and further comprises a subset of isoacceptor tRNAs specific for a second amino acid encoded by the same predetermined codon pair. Each of the isoacceptor tRNAs of the complete set may be labeled with the same donor fluorophore, in which case each of the isoacceptor tRNAs of the subset are labeled with the same acceptor fluorophore. Alternately, each of the isoacceptor tRNAs of the complete set may be labeled with the same acceptor fluorophore, in which case each of the isoacceptor tRNAs of the subset are labeled with the same donor fluorophore.

In a particular embodiment, the complete set is labeled with a plurality of different donor fluorophores and the subset is labeled with a plurality of different acceptor fluorophores. In a particular embodiment, the complete set is labeled with a plurality of different acceptor fluorophores and the subset is labeled with a plurality of different donor fluorophores.

The system may comprise a plurality of isoacceptor tRNAs specific for one amino acid encoded by a predetermined codon. In some cases, each of the isoacceptor tRNAs specific for one amino acid will be labeled with the same donor fluorophore. In a particular embodiment, each of the isoacceptor tRNAs specific for one amino acid will be labeled with the same acceptor fluorophore. In a particular embodiment, the plurality of isoacceptor tRNAs specific for one amino acid will be labeled with a plurality of different acceptor fluorophores. In a particular embodiment, the plurality of isoacceptor tRNAs specific for one amino acid will be labeled with a plurality of different donor fluorophores.

The system may comprise a first plurality of isoacceptor tRNAs specific for a first amino acid that is encoded by one codon of a predetermined codon pair, and further comprise a second plurality of isoacceptor tRNAs specific for a second amino acid that is encoded by the other codon of the same predetermined codon pair. The first plurality may be labeled with the same donor fluorophore, in which case the second plurality is labeled with the same acceptor fluorophore. Alternately, the first plurality may be labeled with the same acceptor fluorophore, in which case the second plurality is labeled with the same donor fluorophore. The first plurality of isoacceptor tRNAs may be labeled with a plurality of different donor fluorophores, in which case the second plurality of isoacceptor tRNAs is labeled with a plurality of different acceptor fluorophores. The first plurality of isoacceptor tRNAs may be labeled with a plurality of different acceptor fluorophores, in which case the second plurality of isoacceptor tRNAs is labeled with a plurality of different donor fluorophores.

One member of any one tRNA pair can be capable of reading one codon of each of a plurality of predetermined codon pairs.

One member of any one tRNA pair can be capable of reading synonymous codons encoding a particular amino acid.

The codons read by the tRNA pair together correspond to an adjacent codon pair, and the occurrence of the adjacent codon pair within an mRNA transcript encoding the protein of interest may be at a frequency that is relatively higher, as compared to the frequency of the translation product of the same codon pair in the proteome of the cell or a subcellular compartment thereof. In a particular embodiment, the translation of the same codon pair in the proteome is at a given time point.

In other particular embodiments, the adjacent codon pair occurs within an mRNA transcript encoding the protein of interest at a frequency that is relatively higher, as compared to the frequency of the same adjacent codon pair in the transcriptome of the cell or a subcellular compartment thereof.

The system may comprise two or more tRNA pairs labeled with two or more FRET pairs. In a particular embodiment, the system comprises two tRNA pairs, and each of the codon pairs translated by the respective tRNA pairs occurs at a frequency in the mRNA encoding the protein that is relatively higher, as compared to the frequency of the translation product of the same codon pairs in the proteome of the cell. In a particular embodiment, the frequency comparison relative to the proteome of the cell is that determined at a given time point.

In a particular embodiment, the system comprises two tRNA pairs, and each of the codon pairs translated by the respective tRNA pairs occurs at a frequency in the mRNA encoding the protein that is relatively higher, as compared to the frequency of the same codon pairs in the transcriptome of the cell.

The system may comprise two different tRNA pairs, wherein each tRNA pair corresponds to a distinct codon pair, and each distinct codon pair occurs in one of two different mRNAs which respectively encode two different proteins of interest. The system may comprise two different tRNA pairs and two different mRNAs, the latter of which respectively encode two different proteins of interest. In this embodiment, each tRNA pair corresponds to a distinct codon pair within one of the two different mRNAs.

In the system comprising two different tRNA pairs and two different mRNAs, each codon pair may occur in its respective mRNA at a frequency that is relatively higher, as compared to the occurrence of the translation product of the same codon pair in the proteome of the cell. The frequency comparison relative to the proteome of the cell may be that determined at a given time point.

In a particular embodiment, one tRNA pair corresponds to a codon pair which occurs in its respective mRNA at a frequency that is relatively higher, as compared to the frequency of the translation product of the same codon pair in the proteome of the cell. In a particular embodiment, the frequency of the translation product of the same codon pair in the proteome is that determined at a given time point.

According to a particular embodiment, the present invention provides a system for measuring translation of a predetermined tRNA pair sequence within a protein of interest, the system comprising a cell or subcellular compartment, wherein the cell or subcellular compartment comprises a nucleic acid sequence encoding the protein of interest, and wherein the cell further comprises a first tRNA labeled with a donor fluorophore and a second tRNA labeled with an acceptor fluorophore, wherein donor and acceptor fluorophores from a FRET pair In one embodiment, the cell being assayed is an intact cell.

In particular embodiments, the system is utilized for measuring the level of translation of the tRNA pair of interest; subsequently, proteins of interest whose tRNA sequence contains the tRNA pair may be identified. In another embodiment, translation of one or more particular proteins of interest whose tRNA sequence contains the tRNA pair is assessed.

In another embodiment, the present invention provides a system for measuring translation of a protein of interest, the system comprising a subcellular compartment, wherein the subcellular compartment comprises (i) an mRNA transcript encoding the protein of interest, and (ii) a first tRNA labeled with a donor fluorophore and a second tRNA labeled with an acceptor fluorophore, and wherein the codon pair recognized by the first and second tRNA occur adjacently in the codon sequence of the mRNA transcript at a frequency higher than the frequency of the same codon pair in the transcriptome of the subcellular compartment.

In a particular embodiment, the tRNA pair defined by the first and second tRNA occur in the tRNA sequence of the protein of interest at a frequency higher than the frequency of the translation product of the same tRNA pair in the proteome of the cell. Thus, the system is capable of producing a FRET signal that is enriched during translation of the transcript of interest, relative to general translation in the subcellular compartment being assayed.

In another embodiment, the adjacent occurrence of the codons read by the first and second tRNA is enriched in the transcript of interest, relative to the transcriptome of the subcellular compartment.

In another embodiment, the invention provides a system for measuring translation of a protein of interest, the system comprising a subcellular compartment, wherein the subcellular compartment comprises (i) a nucleic acid sequence encoding the protein of interest; and (ii) a first tRNA labeled with a donor fluorophore and a second tRNA labeled with an acceptor fluorophore, and wherein the tRNA pair defined by the consecutive order of the first tRNA and the second tRNA occurs in the tRNA sequence of the protein of interest at a frequency higher than the frequency of the translation product of the same tRNA pair in the proteome of that subcellular compartment Reference herein to a "tRNA labeled with a donor fluorophore" or to a "tRNA labeled with a acceptor fluorophore" refers to tRNA molecules directly labeled with the specified fluorophore, and is distinct from tRNA molecules acylated with an amino acid analogue containing a fluorophore.

In particular embodiments of methods and systems of the present invention, a nucleic acid sequence of the gene encoding the protein in the cell or subcellular compartment has been altered so as to increase the frequency of the tRNA pair in the corresponding tRNA sequence of the protein. In another embodiment, a method of the present invention further comprises the step of engineering a gene encoding a protein of interest to increase the frequency of adjacent codons that are read by the tRNA pair of interest.

In another embodiment, the present invention provides a system for measuring utilization of a tRNA pair of interest in protein synthesis, the system comprising a cell or subcellular compartment, wherein the cell or subcellular compartment comprises (i) an mRNA encoding a protein of interest, and (ii) a first tRNA labeled with a donor fluorophore and a second tRNA labeled with an acceptor fluorophore, and wherein the first and second tRNA together form the tRNA pair of interest. In one embodiment, the cell being assayed is an intact cell.

In another embodiment of methods and systems of the present invention, the tRNA pair whose utilization is measured recognize codons which occur adjacently in an mRNA encoding a protein of interest, and this adjacent codon pair occurs in the mRNA encoding the protein of interest at a frequency that is relatively higher, as compared to the frequency of the same codon pair in the transcriptome of the cell or subcellular compartment being assayed. Thus, the FRET signal is enriched during translation of the protein of interest, relative to the signal produced by general translation in the cell being assayed.

A frequency of a codon pair or a translation product thereof, or of a tRNA pair, that is denoted as "significantly higher" or "relatively higher" in comparison to a reference frequency of the same pair in the proteome or transcriptome of the cell or subcellular compartment refers, in particular embodiments, to a frequency that is at least two-fold higher than the frequency in the reference proteome or transcriptome; or at least three-fold higher; or least four-fold higher; or at least five-fold higher; or least six-fold higher; or at least eight-fold higher; or at least 10-fold higher; or at least 15-fold higher; or at least 20-fold higher; or at least 30-fold higher; or at least 50-fold higher; or at least 100-fold higher.

A non-limiting example of a tRNA pair enriched in a protein of interest is the tRNA pair where the first tRNA is capable of being charged with the amino acid Methionine (M) and the second with the amino acid Tryptophane (W). There is a single tRNA species for M and a single tRNA for W. This dipeptide is about 16-fold more abundant in the tRNA sequence of proinsulin than in the human proteome, and the corresponding codon pair is similarly more abundant in the transcript encoding proinsulin than in the human transcriptome. Each possibility represents a separate embodiment of the present invention.

By way of example, once a cell has been labeled according to the principles of the invention to monitor production of a protein of interest, it is possible to compute the confidence of the resulting assay. That is, upon detection and measurement of a FRET signal, it is possible to determine the confidence that the protein of interest is indeed being translated. This requires (a) an estimate of the enrichment E of the selected tRNA pair compared to the average, or background proteins; and (b) an estimate of the fraction f of the rate of production of the protein of interest out of the entire protein production in that cell or tissue. For example, in the case of insulin, we have E=16 and we estimate f=0.25.

To compute the confidence, the tRNA pair of choice is assumed to appear at a frequency $f_d$ in the background proteins; therefore the rate of FRET signal generation by background protein production is proportional to $f_d*(1-f)$, and the rate of FRET signal generation by production of the protein of choice is proportional to $E*f_d*f$. Therefore the probability that an observed signal is due to production of the protein of choice is $E*f_d*f/(E*f_d*f+f_d*(1-f))=Ef/(Ef+1-f)$. In the case of insulin, this becomes $16*0.25/(16*0.25+0.1)=4/4.1=97.5\%$ confidence that insulin is being produced.

Estimation of the enrichment factor E can be performed in several ways. E is computed by comparing the rate of appearance of a specific tRNA pair in a protein of choice with its appearance in all other proteins produced by a cell or tissue. The rate of appearance of a specific tRNA pair in a protein of interest can be computed from the protein sequence. To analyze this rate in the proteome of a cell, one of several strategies can be employed. First, given the genome of that organism, the entire genome can be used as an estimation of the proteins produced by the cell. If additional information is available, for example if proteins specifically produced by that cell type or tissue are known, than this information can be used in addition or alternately. Finally, the average rate of FRET production by that tRNA pair can be measured directly, with and without the protein of interest, such as in cases where the protein of interest is being transfected into cells.

These analyses can be performed either by analyzing amino acid sequences or tRNA sequences, to obtain an optimal labeling strategy either with all isoaccepting tRNAs of a given amino acid or by single moiety tRNAs.

In addition, the sequence of proteins to be produced can sometimes be edited or altered to achieve various benefits. If such edits are permissible, a specific motif can be inserted into the sequence to ensure high confidence identification of the production of the protein of interest. For example, the amino acid pairs. WW and CW occur very rarely in the mouse proteome. A poly-W or poly-CW tail or tag engineered to be expressed within or at a terminus of a protein of interest will ensure confident identification of production of this protein in WW labeled murine cells and tissues. For purposes of illustration, calculations are provided herein for several proteins of interest. In one example, filgrastim is a recombinant human G-CSF (Granulocyte colony stimulating factor), marketed by Amgen under the brand name Neupogen™. This is a 175 residue recombinant protein produced in E. coli.

Analysis of the amino acid sequence of filgrastim and the sequences of all E. coli protein sequences shows that the amino acid pairs CL and LC (Cysteine and Leucine) appear a total of 4 times in the sequence of the target protein (filgrastim) and 3216 times in the background (entire amino acid sequence of E. coli proteins, which includes a total of 1,328,825 dipeptides). Computation of the enrichment factor E yields $E(C,L)=(4/174)/(3216/1,328,825)=9.50$.

In another example, somatotropin is a recombinant human growth hormone with 190-191 residues, marketed by various vendors under several brand names. It is synthesized in E. coli.

Analysis of the amino acid sequence of somatotropin and the sequences of all E. coli protein sequences shows that the amino acid pairs CF and FC (Cysteine and Phenylalanine) appear a total of 2 times in the sequence of the target protein (somatotropin) and 1388 times in the background. Computation of the enrichment factor yields $E(C,F)=(2/190)/(1388/1,328,825)=10.08$.

In another example, human serum alanine aminotransferase (ALT) is regarded as an indicator of liver damage based on the presumption that ALT protein is specifically and abundantly expressed in the liver. ALT 1 and ALT 2 are two homologous isoforms with 70% identity and 85% similarity. Analysis of the tRNA sequences of ALT 1, ALT 2 and the human genome considered as a background or average protein identifies several tRNAs pairs that are specific to ALT 1 but not ALT 2 or background, and several tRNAs pairs that are specific to ALT 2 but not Alt1 or background, as shown in Table 2. In addition, numerous tRNA pairs out of the total of 1225 possible tRNA pairs can be found which are represented in the background but not in either ALT 1 or ALT 2. This example illustrates the ability to use tRNA pairs for simultaneously monitoring more than one protein and distinguishing these proteins from each other and from the background, even in case of significant homology.

TABLE 2

| tRNA pair | Frequency in background | Frequency in Alt1 | Frequency in Alt2 | Enrichment factor |
|---|---|---|---|---|
| Arg4Ala2 | 0.000131 | 0.004032 | 0 | 30.81001 |
| Pro2Arg1 | 0.000271 | 0.004032 | 0 | 14.90603 |
| Tyr2Ser2 | 0.000147 | 0.002016 | 0 | 13.72198 |
| Arg2Arg2 | 0.000308 | 0 | 0.005736 | 18.60601 |
| Ala2Tyr2 | 0.000133 | 0 | 0.001912 | 14.37869 |
| Arg2Ser3 | 0.000138 | 0 | 0.001912 | 13.83889 |

In another example, etanercept is a dimeric fusion protein consisting of the extracellular ligand-binding portion of the human 75 kiloDalton (p75) tumor necrosis factor receptor (TNFR) linked to the Fc portion of human IgG1. Etanercept is produced by recombinant DNA technology in a Chinese hamster ovary (CHO) mammalian cell expression system. It consists of 467 amino acids. It is marketed by Immunex under the brand name of Enbrel™. To determine the best labeling strategy, the mouse genome was used as an approximation to the unavailable proteome of CHO cells, since the Chinese Hamster and mouse have a very similar genomic structure. Analysis of the amino acid sequence of etanercept and the sequences of all mouse protein sequences shows that the amino acid pairs WN and NW (Asparagine and Tryptophan) appear a total of 4 times in the sequence of the target protein and 8313 times in the background.

Computation of the enrichment factor E yields:

$$E(W,N)=(4/466)/(11644/11,638,331)=8.58.$$

In another example, cetuximab is an epidermal growth factor receptor binding FAB. Cetuximab is composed of the Fv (variable; antigen-binding) regions of the 225 murine EGFr monoclonal antibody specific for the N-terminal portion of human EGFr with human IgG1 heavy and kappa light chain constant (framework) regions. It is marketed by ImClone™ systems under the brand name of Erbitux™. To determine the best labeling strategy, the mouse genome was used as an approximation to the unavailable proteome of CHO cells. Analysis of the 452-long amino acid sequence of heavy-chain I of cetuximab and the sequences of all mouse protein sequences shows that the amino acid pairs WY and YW (Tyrosine and Tryptophan) appear a total of 2 times in the sequence of the target protein and 17296 times in the background. Computation of the enrichment factor E yields $E(Y,W)=(2/451)/(8313/11,638,331)=6.21$.

In another embodiment, comparison of the sequence of the specific protein to the sequences of background proteins is performed on the basis of adjacent tRNA pairs. In this analysis, two histograms are prepared of all consecutive pairs of tRNAs in the protein of interest and in all background proteins. In this histogram, directionality is disregarded; that is, $R_5L_3$ and $L_3R_5$ are considered identical. In Homo sapiens, there are 49 distinct tRNAs (including selenocysteine), so that this histogram contains (49*49+49)/2=1225 entries. This is reached as follows: (49*49−49)/2 is the number of hetero-tRNA-pairs, and 49 is the number of homo-tRNA-pairs (both member have the same species, where one member is labeled with the donor and the other with the acceptor fluorophore of the FRET pair). The number of possible pairs is thus (49*49−49)/2+49=(49*49+49)/2=49*50/2=1225.

In another embodiment, comparison of the sequence of the specific protein to the sequences of background proteins is performed on the basis of adjacent amino acid pairs. In this analysis, two histograms are prepared of all consecutive pairs of amino acids in the protein of interest and in all background proteins. In this histogram, directionality is disregarded; that is, FY and YF are considered identical. This histogram contains (20*20+20)/2=210 entries. This is reached as follows: (20*20−20)/2 is the number of hetero-dipeptides, and 20 is the number of homo-dipeptides (peptides can be labeled both as donor and acceptor). The number of possible pairs is thus (20*20−20)/2+20=(20*20+20)/2.

After this histogram is determined, it is normalized so that the sum of all its entries becomes equal to unity. Then, the two histograms are compared by dividing the value of the entry in the histogram for the protein of interest by the corresponding entry for the background proteins. The entry provides the significance value for that amino acid pair. The entry with the highest factor is a leading candidate for use in a method of the present invention. The assay herein disclosed can be further enhanced by using more than one tRNA pair, either simultaneously in the same cell or cells (by using distinct spectral properties of the various pairs) and/or separately, for example in different wells of a multi-well assay plate. In this way, if a single tRNA pair provides an assay for production of a protein of interest with confidence of C1, and if another assay with a distinct pair provides a confidence of C2, than the combination of these two assay provides confidence of 1−(1−C1)*(1−C2). Clearly, this concept can be generalized up to the maximal number of bi-markers, 210 pairs for the case of amino-acid isoaccepting tRNA sets, or N*(N+1)/2 for N tRNA moieties, where N=49 for Homo sapiens cells, N=20 for Homo sapiens mitochondria and so on for each case.

In various embodiments, a cell or subcellular compartment of a system of the present invention further comprises a second tRNA pair labeled with a second FRET pair i.e. a third tRNA labeled with a second donor fluorophore and a fourth tRNA labeled with a second acceptor fluorophore (collectively termed a "second tRNA pair labeled with a second FRET pair"). Either or both of the first and second tRNA pairs may correspond to pairs of adjacent tRNAs which occur in the tRNA sequence of the protein of interest at a frequency significantly higher than the frequency of the same pair in the proteome of the cell or subcellular compartment. The third and fourth tRNA thus produce a second FRET signal distinct from the FRET signal produced by the first and second tRNA of the first tRNA pair. In this embodiment, the emission spectrum of the second donor fluorophore overlaps with the excitation spectrum of the second acceptor fluorophore. In this embodiment, the second FRET signal reflects general translation in the cell or subcellular compartment being assayed, not including translation of the transcript of interest.

In another embodiment, translation of the transcript of interest makes a relatively small contribution to the second FRET signal which can be computed and factored out. In either case, analysis of the first and second FRET signals enables accurate determination of the level of translation of the protein of interest.

In another embodiment, the frequency of the adjacent codons corresponding to the third and fourth tRNA is significantly lower in the transcript of interest, relative to the transcriptome of the cell or subcellular compartment. Each possibility represents a separate embodiment of the present invention.

In another embodiment, a system of the present invention further comprises an additional cell, the additional cell comprising a second tRNA pair labeled with a second FRET pair, wherein the second tRNA pair corresponds to a pair of adjacent tRNAs which occurs in the tRNA sequence of the protein of interest at a frequency significantly higher than the frequency of the translation product of the same pair in the proteome of the cell.

In another embodiment, the additional cell is substantially identical to the cell containing the first tRNA pair. The second FRET pair comprises a second donor fluorophore and a second acceptor fluorophore, wherein the emission spectrum of the second donor fluorophore overlaps with the excitation spectrum of the second acceptor fluorophore. In this embodiment, the FRET signal from the second tRNA pair reflects general translation in the cell being assayed, not including translation of the transcript of interest. In another embodiment, the adjacent occurrence of codons corresponding to the third and fourth tRNA is significantly lower in the transcript of interest, relative to the transcriptome of the cell. Each possibility represents a separate embodiment of the present invention.

In another embodiment, a system of the present invention further comprises an additional subcellular compartment, the additional subcellular compartment comprising a second tRNA pair labeled with a second FRET pair, wherein the second tRNA pair corresponds to a pair of adjacent tRNAs which occurs in the tRNA sequence of the protein of interest at a frequency significantly higher than the frequency of the translation product of the same pair in the proteome of the subcellular compartment. In another embodiment, the additional subcellular compartment is substantially identical to the subcellular compartment containing the first tRNA pair. The second FRET pair comprises a second donor fluorophore and a second acceptor fluorophore, wherein the emission spectrum of the second donor fluorophore overlaps with the excitation spectrum of the second acceptor fluorophore. In this embodiment, the FRET signal from the second tRNA pair reflects general translation in the subcellular compartment being assayed, not including translation of the transcript of interest.

In another embodiment, the frequency in the transcript of interest of a codon pair corresponding to the first tRNA pair is significantly lower in said transcript, relative to the frequency of the same codon pair in the transcriptome of the subcellular compartment.

In another embodiment, FRET signals emitted from the first and second labeled tRNA pairs (also referred to respectively as the "first" and "second FRET signals") of the present invention are capable of being analyzed together in order to increase the accuracy of measurement of translation of a transcript of interest. In another embodiment, analysis of the first and second FRET signals together enables more accurate determination of the contribution of background translation (translation of transcripts other than the transcript of interest), thereby increasing the signal-to-noise ratio of measurement of the transcript of interest. Each possibility represents a separate embodiment of the present invention.

In another embodiment of methods and systems of the present invention, the sequence of the gene encoding the protein in the cell or subcellular compartment has been altered to increase the frequency of the codon pair corresponding to the third and fourth tRNA pair.

It will be understood by those of skill in the art that, in an instance wherein the third and fourth tRNAs introduced to a sample that is different from the sample containing the first and second tRNAs, the second donor fluorophore may be the same as or different from the first donor fluorophore of the present invention. In an instance wherein the first, second, third, and fourth tRNAs are all present in the same biological sample, the second donor fluorophore must have an excitation or emission spectrum distinct from that of the first donor fluorophore. In another embodiment, the emission or excitation spectra of the first and second donor fluorophores can overlap, but must not be identical, and it should preferably be possible to separate their contributions to FRET signals generated by the biological sample. Each possibility represents a separate embodiment of the present invention.

Similarly, it will be understood that, in an instance wherein the third and fourth tRNAs (i.e. the second tRNA pair) are present in a sample different from the sample containing the first and second tRNAs (i.e. the first tRNA pair), the second acceptor fluorophore may be the same as or different from the first acceptor fluorophore of the present invention. In an instance wherein the first, second, third, and fourth tRNAs are all present in the same biological sample, the second acceptor fluorophore must have an excitation or absorption spectrum distinct from the first acceptor fluorophore. In another embodiment, the excitation and absorption spectra of the first and second acceptor fluorophores can overlap, but must not be identical, and in preferable embodiments, their contributions to FRET signals generated by the biological sample are distinguishable and separated.

In another embodiment, a plurality of cells or subcellular compartments comprising the labeled element is utilized in a system of the present invention.

In another embodiment, the present invention provides a method for sorting a cell population based on its expression level of a protein, the method comprising the steps of performing a method of the present invention, measuring the signals produced thereby, and sorting the cells.

In another embodiment, the present invention provides a method for enriching a cell population based on its expression level of a protein, the method comprising the steps of performing a method of the present invention, measuring the signals produced thereby, and enriching for those cells with increased expression of the protein of interest.

In another embodiment, the present invention provides a method for screening cell populations based on their expression levels of a protein, the method comprising the steps of performing a method of the present invention, measuring the signals produced thereby, and identifying cell populations with increased expression of the protein of interest. In another embodiment, the cell populations are clonal populations. In another embodiment, the method is a high-throughput screening method. Each possibility represents a separate embodiment of the present invention.

In another embodiment, the system of the present invention further comprises instructions for use thereof in measuring or monitoring translation of a protein of interest in an intact cell or a cellular organelle.

In another embodiment, the invention provides a method for measuring translation of a protein of interest in a biological sample comprising at least one cell, the method comprising the steps of:
 (i) selecting a specific tRNA pair which occurs in the tRNA sequence of a protein of interest at a known frequency;
 (ii) introducing into the biological sample a tRNA pair labeled as a FRET pair, wherein an acceptor fluorophore and a donor fluorophore together form the FRET pair and wherein each member of the tRNA pair is labeled with one of the acceptor fluorophore or the donor fluorophore, and wherein the tRNA pair corresponds to a consecutive pair of codons in the mRNA of the protein of interest; and
 (iii) detecting FRET signals emitted from the biological sample during protein translation, thereby measuring translation of the protein of interest.

The frequency of the tRNA pair in the tRNA sequence of a protein may be known to be higher or lower than the frequency of its corresponding translation product in the proteome of the cells of the biological sample. In a particular embodiment, a second tRNA pair is introduced to the sample. The second tRNA pair may be introduced into a cell or subcellular compartment that is other than that into which the first tRNA pair is introduced. In the case of either or both of the first tRNA pair and second tRNA pair, opposite orientations of the particular pair may occur in adjacent positions in the tRNA sequence of the protein of interest. In the case of either or both of the first tRNA pair and second tRNA pair, opposite orientations of the particular pair may occur in overlapping positions in the tRNA sequence of the protein of interest.

There is further provided a method for measuring translation of a protein of interest in a biological sample comprising at least one cell, the method comprising the steps of:
 (i) selecting a first codon pair which occurs in the mRNA sequence encoding a protein of interest at a known frequency;
 (ii) introducing into the biological sample comprising cells at least one first tRNA pair, wherein for each first tRNA pair, each tRNA member of the tRNA pair is capable of reading one codon of the first codon pair selected in (i); and wherein one tRNA member of the tRNA pair is labeled with a donor fluorophore and the other member of the tRNA pair is labeled with an acceptor fluorophore, and wherein the donor fluorophore and the acceptor fluorophore together form a FRET pair; and
 (iii) detecting FRET signals emitted from the tRNA pair during protein translation, thereby measuring translation of the protein of interest.

The codon pair selected in (i) may occur in the mRNA sequence at a frequency that is relatively higher, as compared to the frequency of the translation product of the same codon pair in the proteome of the cell or subcellular compartment thereof comprising the biological sample. In particular embodiments, the frequency of said translation product in the proteome is that determined at a given time point.

In a particular embodiment, the method further comprises a step of altering the nucleic acid sequence of the gene encoding the protein of interest so as to increase the frequency of the codon pair in the mRNA sequence encoding the protein.

In a particular embodiment, the method further comprises:
 (iv) selecting a second codon pair, wherein the second codon pair occurs in the mRNA sequence encoding the protein of interest at a relatively higher frequency as compared to the frequency of the translation product of the second codon pair in the proteome of the biological sample; and (v) introducing into the biological sample at least one second tRNA pair, wherein each tRNA member of the second tRNA pair is capable of reading one codon of the second codon pair selected in (iv), and wherein each tRNA member of the second tRNA pair is labeled with either a second donor fluorophore or a second acceptor fluorophore, and wherein the second donor fluorophore and the second acceptor fluorophore together form a second FRET pair.

In a particular embodiment, at least one of the acceptor fluorophore and the donor fluorophore of the second FRET pair is other than that of the first FRET pair. In a particular embodiment, the acceptor fluorophore and the donor fluorophore of the second FRET pair are both other than that of the first FRET pair.

In a particular embodiment, the method further comprises altering a nucleic acid sequence of the gene encoding the protein so as to increase the frequency of the second codon pair in the mRNA sequence encoding the protein of interest.

In a particular embodiment, opposite orientations of the second codon pair occur in adjacent positions in the mRNA sequence encoding the protein of interest.

The introducing of the second tRNA pair in (v) may be into a cell or subcellular compartment that is other than that of the introducing of the first tRNA pair in (ii).

In one embodiment, the codon pair selected in (i) is one which occurs in the mRNA sequence of the protein of interest at a frequency that is relatively higher, as compared to the frequency of the translation product of the same codon pair in the proteome of a subcellular compartment of the biological sample, and the introducing of the tRNA pair in (ii) is into the subcellular compartment.

The biological sample may be selected from the group consisting of a cell line, a primary cell culture, a whole organism or a subcellular compartment thereof. The step of introducing can be performed in cells, such as mammalian cells, vertebrate cells, avian cells, insect cells, yeast cells and plant cells. The mammalian cells may be human cells or non-human mammalian cells. In a particular embodiment, the biological sample comprises diseased cells. In a particular embodiment, the step of introducing is into a subcellular compartment of living ZS cells. The subcellular compartment may be selected from dendritic spines, mitochondria, endoplasmic reticulum (ER) and chloroplasts.

The whole organism may be a model organism used for genetic research, such as *Escherichia. coli, Caenorhabditis elegans, Drosophila melanogaster, Arabidopsis thaliana*, and an inbred strain of *Mus musculus*. The model organism may be any other model organism used for genetic research.

The cells used in the system and methods of the invention may be live or fixated cells. Fixated cells may additionally be permeabilized. Methods for chemically fixating cells are well known in the art and include in general, use of organic solvents and/or cross-linking reagents. Organic solvents used for fixation include various alcohols, acetone and acetic acid. Cross-linking reagents used for fixation include various aldehydes, such as formalin and paraformaldehyde. Cross-linking reagents form intermolecular bridges and thus may be preferable over certain organic solvents for preserving cell structure. Other agents used for chemical fixation include for example, oxidizing agents, mercurial compounds, picrates, HOPE fixative (Hepes-glutamic acid buffer-mediated organic solvent protection effect)

According to other embodiments, the biological sample comprises mitochondria and at least one of said first tRNA and said second tRNA is a mitochondria-specific tRNA. In other embodiments, both said first tRNA and said second tRNA are a mitochondria-specific tRNA. Each possibility represents a separate embodiment of the present invention.

According to other embodiments, the step of introducing is into mitochondria and the tRNA pair comprises at least one mitochondria-specific tRNA. In other embodiments, both members of the tRNA pair are mitochondria-specific tRNA.

In a particular embodiment, the method further comprises a step of irradiating the biological sample with electromagnetic radiation prior to the step of measuring the emitted electromagnetic radiation, wherein the electromagnetic radiation used for irradiating is of a wavelength different from the detected FRET signals.

In a particular embodiment, the method further comprises a step of altering the nucleic acid sequence of the gene encoding the protein of interest so as to increase the frequency of the tRNA pair in the tRNA sequence of the protein.

In another embodiment, the present invention provides a method for measuring translation of a transcript of interest in a cell, the method comprising the steps of:
  (i) introducing into a cell a first tRNA and a second tRNA, wherein the first tRNA is labeled with a donor fluorophore, and the second tRNA is labeled with an acceptor fluorophore, wherein the cell comprises the transcript of interest, and wherein the adjacent codon pair recognized by the first tRNA and the second tRNA occurs in the codon sequence of the transcript of interest at a frequency significantly higher than the frequency of the same codon pair in the transcriptome of the cell; and
  (ii) detecting FRET signals emitted from the cell.

In another embodiment, the present invention provides a method for measuring translation of a transcript of interest in a subcellular compartment, the method comprising the steps of:
  (i) introducing into a subcellular compartment a first tRNA and a second tRNA, wherein the first tRNA is labeled with a donor fluorophore, and the second tRNA is labeled with an acceptor fluorophore, wherein the subcellular compartment comprises the transcript of interest, and wherein the adjacent codon pair recognized by the first tRNA and the second tRNA occurs in the codon sequence of the transcript of interest at a frequency significantly higher than the frequency of the same codon pair in the transcriptome of the subcellular compartment; and
  (ii) detecting FRET signals emitted from the subcellular compartment.

In another embodiment, the adjacent occurrence of the first and second tRNA is enriched in the transcript of interest, relative to the transcriptome of the subcellular compartment. In another embodiment, the subcellular compartment is an organelle.

In other embodiments, a method of the present invention is used to measure translation of a protein of interest in a cell or subcellular compartment. In this embodiment, the first tRNA and second tRNA of the present invention are present in the tRNA sequence of the protein of interest at a frequency significantly higher than the frequency of the corresponding codon in the transcriptome of the cell or subcellular compartment; or at a frequency significantly higher than the frequency of the corresponding translation product in the proteome. Each possibility represents a separate embodiment of the present invention.

In one embodiment, the method for measuring translation of a protein of interest in a biological sample comprises the steps of:
  (i) selecting one or more tRNA pairs which occurs in the tRNA sequence of the protein of interest at a known frequency, wherein each tRNA pair is defined by a first set of tRNA and a second set of tRNA;

(ii) introducing into a biological sample the first set of tRNA and the second set of tRNA, wherein the tRNA in the first set are labeled with a donor fluorophore, and the tRNA in the second set are labeled with an acceptor fluorophore, and wherein the biological sample further comprises a nucleic acid sequence encoding the protein of interest, and wherein the frequency of the occurrence of the tRNA pair in the tRNA sequence of the protein of interest is higher than the frequency of the translation product of the tRNA pair in the proteome of the cell; and (iii) detecting FRET signals radiation emitted from the biological sample, thereby measuring translation of the protein of interest.

In another embodiment, the present invention provides a method for measuring the effect of a drug candidate on translation of a transcript of interest, the method comprising the steps of:

(i) introducing into a intact cell a first tRNA and a second tRNA, wherein the first tRNA and second tRNA are labeled with a donor fluorophore, and an acceptor fluorophore, respectively, wherein the cell comprises the transcript of interest, and wherein the adjacent codon pair recognized by the first and second tRNA occurs in the codon sequence of the transcript of interest at a frequency significantly higher than the frequency of the translation product of the same codon pair in the proteome of the cell;

(ii) measuring electromagnetic radiation emitted from the acceptor fluorophore;

(iii) contacting the cell with the drug candidate; and (iv) measuring electromagnetic radiation emitted from the cell, under the conditions of (iii), whereby a significant difference between the electromagnetic radiation measured in step (ii) and the electromagnetic radiation measured in step (iv) indicates that the drug candidate affects the translation of a transcript of interest.

Step (ii) is performed under conditions wherein the cell has not been contacted with the drug candidate. It will be understood to those of skill in the art that the cell can comprise the transcript of interest by virtue either of the presence therein of DNA that encodes the transcript of interest or by transfection of the transcript of interest into the cell. Each possibility represents a separate embodiment of the present invention.

In another embodiment, the present invention provides a method for measuring the effect of a drug candidate on translation of a transcript of interest, the method comprising the steps of:

(i) introducing into a subcellular compartment a first tRNA and a second tRNA, wherein the first tRNA and second tRNA are labeled with a donor fluorophore, and an acceptor fluorophore, respectively, wherein the subcellular compartment comprises the transcript of interest, and the adjacent codon pair recognized by the first and second tRNA occurs in the codon sequence of the transcript of interest at a frequency significantly higher than the frequency of the translation product of the same codon pair in the proteome of the subcellular compartment;

(ii) measuring electromagnetic radiation emitted from the subcellular compartment;

(iii) contacting the subcellular compartment with the drug candidate; and (v) measuring electromagnetic radiation emitted from the subcellular compartment, under the conditions of (iii), whereby a significant difference between the electromagnetic radiation measured in step (ii) and the electromagnetic radiation measured in step (iv) indicates that the drug candidate affects the translation of a transcript of interest.

Step (ii) is performed under conditions wherein the subcellular compartment has not been contacted with the drug candidate. It will be understood to those of skill in the art that the subcellular compartment can comprise the transcript of interest by virtue either of the presence therein of DNA that encodes the transcript of interest or by transfection of the transcript of interest into the subcellular compartment. Each possibility represents a separate embodiment of the present invention.

In another embodiment, step (iv) of one of the above methods is performed immediately after administration of the drug candidate. In another embodiment, an equilibration period of 5-120 minutes is allowed prior to the translation assay. In another embodiment, step (iv) is performed at a time wherein the drug candidate is still present in effective quantities. In another embodiment, step (iv) is performed at a time wherein the first and second labeled tRNA are still present in quantities substantially equivalent to those in step (ii). In another embodiment, the first and second labeled tRNA are re-administered to the biological sample in order to be present in quantities substantially equivalent to those in step (ii). Each possibility represents a separate embodiment of the present invention.

In another embodiment, the present invention provides a method for measuring the effect of a drug candidate on translation of a transcript of interest, the method comprising the steps of:

(i) introducing into each of a first cell preparation and a second cell preparation a first tRNA and a second tRNA, wherein the first and second tRNA are labeled with a donor fluorophore and an acceptor fluorophore, respectively, and wherein each of the first cell preparation and the second cell preparation comprise the transcript of interest, and the adjacent codon pair recognized by the first and second tRNA occurs in the codon sequence of the transcript of interest at a frequency significantly higher than the frequency of the translation product of the same codon pair in the proteome of the cells;

(ii) introducing to the second cell preparation a drug candidate;

(iii) measuring electromagnetic radiation emitted from the first cell preparation; and (iv) measuring electromagnetic radiation emitted from the second cell preparation, wherein a significant difference between the electromagnetic radiation measured in step (iii) and the electromagnetic radiation measured in step (iv) indicates that the drug candidate affects the translation of the transcript of interest.

Step (iii) is performed under conditions wherein the first cell preparation has not been contacted with the drug candidate. It will be understood to those of skill in the art that the cells can comprise the transcript of interest by virtue either of the presence therein of DNA that encodes the transcript of interest or by transfection of the transcript of interest into the cells. In another embodiment, the second cell preparation is substantially identical to the first cell preparation, except that the second cell preparation has not been contacted with the drug candidate. Each possibility represents a separate embodiment of the present invention.

In another embodiment, the present invention provides a method for measuring the effect of a drug candidate on translation of a transcript of interest, the method comprising the steps of:
(i) introducing into each of a first preparation and a second preparation comprising a subcellular compartment a first tRNA and a second tRNA (i.e. a first tRNA pair), wherein the first and second tRNA are labeled with a donor fluorophore and an acceptor fluorophore, respectively, and wherein each of the first and second preparations comprises the transcript of interest, and the adjacent codon pair recognized by the first and second tRNA occurs in the codon sequence of the transcript of interest at a frequency significantly higher than the frequency of the translation product of the same codon pair in the proteome of the subcellular compartment;
(ii) introducing to the second preparation a drug candidate;
(iii) measuring electromagnetic radiation emitted from the first preparation; and
(iv) measuring electromagnetic radiation emitted from the second preparation, wherein a significant difference between the electromagnetic radiation measured in step (iii) and the electromagnetic radiation measured in step (iv) indicates that the drug candidate affects the translation of a transcript of interest.
Step (iii) is performed under conditions wherein the first preparation of the subcellular compartment has not been contacted with the drug candidate. It will be understood to those of skill in the art that the subcellular compartment can comprise the transcript of interest by virtue either of the presence therein of DNA that encodes the transcript of interest or by transfection of the transcript of interest into the subcellular compartment. In another embodiment, the second preparation is substantially identical to the first preparation, except that the second preparation has not been contacted with the drug candidate. Each possibility represents a separate embodiment of the present invention.

In another embodiment, a method of the present invention further comprises the steps of introducing into the cell or cells being analyzed a second tRNA pair, i.e. a third tRNA labeled with a second donor fluorophore and a fourth tRNA labeled with a second acceptor fluorophore. The adjacent codon pair recognized by the second tRNA pair occurs in the codon sequence of the transcript of interest at a frequency that is significantly lower than the frequency of the translation product of the same codon pair in the proteome of the cell. The labeled second tRNA pair produces a second FRET signal distinct from the FRET signal produced by the labeled first tRNA pair. In this embodiment, the second FRET signal reflects general translation in the cell being assayed, not including translation of the transcript of interest. In another embodiment, translation of the transcript of interest makes a relatively small contribution to the second FRET signal. In either case, analysis of the first and second FRET signals enables accurate determination of the level of translation of the transcript of interest. In another embodiment, the adjacent occurrence of the first and second tRNA is significantly lower in the transcript of interest, relative to the transcriptome of the cell.

In another embodiment, a method of the present invention further comprises the steps of introducing into a cell or subcellular compartment thereof under analysis, a second tRNA pair, i.e. a third tRNA labeled with a second donor fluorophore and a fourth tRNA labeled with a second acceptor fluorophore, wherein the adjacent codon pair recognized by the third tRNA and the fourth tRNA occurs in the codon sequence of the transcript of interest at a frequency significantly lower than in the proteome of the cell or subcellular compartment. The second tRNA pair thus produces a second FRET signal distinct from the FRET signal produced by the first tRNA pair.

In another embodiment, a method of the present invention further comprises the steps of introducing into an additional cell or an additional subcellular compartment a second tRNA pair, i.e. a third tRNA labeled with a second donor fluorophore and a fourth tRNA labeled with a second acceptor fluorophore, wherein the codons recognized by the third tRNA and the fourth tRNA occur adjacently in the codon sequence of the transcript of interest at a frequency that is significantly lower than the frequency of the translation product of the same codon pair in the proteome of the cell or subcellular compartment.

In another embodiment, a method of the present invention further comprises the step of irradiating the system or biological sample with a source of electromagnetic radiation prior to the step of detecting the electromagnetic radiation emitted in the form of FRET signals. This source produces electromagnetic radiation of a different wavelength than that detected as a readout of protein translation activity. In another embodiment, the wavelength of electromagnetic radiation produced by this source is the excitation wavelength of a marker of the present invention. In another embodiment, the wavelength is the excitation wavelength of the donor fluorophore of the FRET pair contained in the first and second tRNA.

In another embodiment, a method of present invention is used to monitor translation of a group of specific proteins. In this embodiment, a method of the present invention is generalized to more than 2 labels, yielding a system of equations is be solved for the unknowns. In another embodiment, all 210 pairs are used, for example in a multi-well plate. The cells at hand are placed in the well plate and the tRNA pairs and required reagents are added. Once the FRET signals have been measured, a computer program analyzes the 210 numbers and outputs the required results. In another embodiment, this method is used to define a protein production profile or "fingerprint," which can then be used for purposes such as quality assurance, cell characterization, and drug development.

According to one embodiment, the method of the present invention further comprises the step of analyzing the electromagnetic radiation or a signal produced therefrom, thereby obtaining a read-out in real-time of the translation of a transcript of interest According to another embodiment, a method of the present invention further comprises the step of computing the number of events (N) over a period of time t, wherein $$N \sim \frac{\sum I_t^2}{\sum \delta I_t^2}$$

wherein $I_t$ is the average signal strength at time t and $\delta I_t$ is the average signal deviation at time t, thereby obtaining a readout of translation of the transcript of interest. "Average signal deviation" refers, in another embodiment, to the detected signal minus the average signal.

In another embodiment, a plurality of cells or subcellular compartments comprising the labeled element is utilized in a method of the present invention.

In one exemplary embodiment, the transcript of interest encodes insulin. In another embodiment, the transcript of interest encodes collagen or elastin. In another embodiment, the transcript of interest encodes a growth factor. In another embodiment, the transcript of interest encodes erythropoietin. In another embodiment, the transcript of interest encodes a stem cell specialization factor. In another embodiment, the transcript of interest encodes a protein selected from insulin, a growth factor, erythropoietin, a stem cell specialization factor and a proteosome inhibitor. Each possibility represents a separate embodiment of the present invention.

In another embodiment, the protein of interest of the present invention is an antibody. In another embodiment, the antibody is a therapeutic antibody. In another embodiment, the antibody is a diagnostic antibody. In another embodiment, the antibody has a known utility selected from a therapeutic utility and a diagnostic utility.

In another embodiment, the protein of interest is selected from the group consisting of insulin, a growth factor, an antibody, erythropoietin, and a stem cell specialization factor. In another embodiment, the transcript of interest encodes another recombinant protein used for a therapeutic purpose. In another embodiment, the transcript of interest encodes another recombinant protein used for a diagnostic purpose. Each possibility represents a separate embodiment of the present invention.

In another embodiment, the protein of interest is selected from the group consisting of CPF-DD, Peptide T, vasoactive intestinal peptide, tetradecapeptide, erythropoietin, insulin, growth hormone, pentigetide, histamine releasing peptide antigen, vasoactive intestinal peptide analog, corticotropin releasing factor, corleukin, CY 725, CY 726, pancreatic trypsin inhibitor, somatostatin, calcium channel peptide, Ebiratide, DGAVP, E-2078, DPDPE, Dynorphin A, sleep inducing peptide, calcitonin, PTH-releasing peptide, growth hormone releasing peptide, HCG, hirudin, an hirudin analog, applagin, corplatin, integrelin, a viper venom polypeptide, desmopressin, antistasin, EGF receptor blocker, Bestatin, buserelin, goserelin, leuprolide, TGF beta, atrial natriuretic peptide, auriculin, brain neuritic peptide, urodilatin, captopril, ACE inhibitor peptide, and a renin inhibitor.

In another embodiment, the protein of interest of the present invention is selected from the group consisting of growth hormone, prolactin, placental lactogen, luteinizing hormone, follicle-stimulating hormone, chorionic gonadotropin, thyroid-stimulating hormone, leptin, adrenocorticotropin, angiotensin I, angiotensin II, beta-endorphin, beta-melanocyte stimulating hormone, cholecystokinin, endothelin I, galanin, gastric inhibitory peptide, glucagon, insulin, lipotropins, neurophysins, somatostatin, calcitonin, calcitonin gene related peptide, beta-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, and thyrotropin releasing hormone.

In another embodiment, the protein of interest of the present invention is selected from the group consisting of carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione beta-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, beta-glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerbrosidase, sphingomyelinase, beta-L-iduronidase, glucose-6-phosphate dehydrogenase, glucosyltransferase, HSV thymidine kinase, and human thymidine kinase.

According to some embodiments, the protein of interest further comprises a protein tag. According to other embodiments, the protein of interest is a fusion protein comprising a protein tag. According to other embodiments, the protein tag is selected from the group consisting of an affinity tag, a solubilization tag, a chromatography tag, an epitope tag and a fluorescent protein tag. It is to be specifically understood that a single protein tag may fall into more than one of the aforementioned categories.

Examples of protein tags include, without limitation, protein A; biotin-carboxy carrier protein (BCCP; SEQ ID NO:1) tag; c-myc tag (EQKLISEEDL; SEQ ID NO:2); calmodulin tag; FLAG-tag (DYKDDDDK; SEQ ID NO:3); IRS (RYIRS; SEQ ID NO:4); AU1 (DTYRYI; SEQ ID NO:5); AU5 (TD-FLYK; SEQ ID NO:6); hemagglutinin (HA) tag; KT3 (KPPT-PPPEPET; SEQ ID NO:7); VSV-G (YTDIEMNRLGK; SEQ ID NO:8); polyhistidine (His-tag); maltose binding protein tag; Nus tag; glutathione-S-transferase (GST) tag; green fluorescent protein (GFP) tag; thioredoxin; S-tag; Strep-tag (WSHPQFEK; SEQ ID NO:9); and T7 tag.

In another embodiment, the present invention provides a method of performing quality assurance of expansion of a stem cell population of interest, wherein the stem cell population expresses a stem cell specialization factor, the method comprising the steps of (i) introducing into the stem cell population a first tRNA and second tRNA, wherein the first tRNA is labeled with a donor fluorophore, the second tRNA is labeled with an acceptor fluorophore, and the adjacent codon pair recognized by the first tRNA and the second tRNA occurs in the codon sequence of a transcript encoding the stem cell specialization factor at a frequency that is significantly higher than the frequency of the translation product of the same codon pair in the proteome of the cell population; and (ii) detecting electromagnetic radiation emitted from the stem cell population. In another embodiment, the adjacent codon pair is enriched in the transcript encoding the stem cell specialization factor, relative to the transcriptome of the cell population.

In another embodiment, the present invention provides a method of performing quality assurance of production of a recombinant protein of interest in a cell population, the method comprising the steps of (i) introducing into the population a tRNA pair comprising a first tRNA and second tRNA, wherein one of the first tRNA or the second tRNA is labeled with a donor fluorophore, and the other is labeled with an acceptor fluorophore, wherein the donor fluorophore and the acceptor fluorophore together form a FRET pair; and wherein the adjacent codon pair recognized by the first tRNA and the second tRNA occurs in the codon sequence of a transcript encoding the recombinant protein at a frequency that is significantly higher than the frequency of the translation product of the same codon pair the proteome of the cell population; and (ii) detecting FRET signals emitted from the cell population. In another embodiment, the adjacent occurrence of the first and second tRNA is enriched in the transcript encoding the recombinant protein, relative to the transcriptome of the cell population.

In another embodiment, the recombinant protein is a fusion protein comprising a protein of interest and a protein tag. In a particular embodiment, the adjacent codon pair recognized by the first tRNA and the second tRNA occurs in the codon sequence of the protein tag. In a particular embodiment, the adjacent codon pair recognized by the first tRNA and the second tRNA occurs in the codon sequence of the mRNA encoding the protein of interest.

In a particular embodiment, the recombinant protein of interest is a recombinant antibody. In another embodiment, the cell population of comprises a recombinant antibody-producing cell population.

In another embodiment, the above method is used to facilitate clone enrichment in the process of isolation of a clone producing a desired amount of the target antibody.

In another embodiment, the above method is used to facilitate clone sorting in the process of isolation of a clone producing a desired amount of the target antibody.

In another embodiment, the present invention provides a method of performing quality assurance of antibody production in a population of a recombinant antibody-producing cell type.

In another embodiment, the antibody of the above methods is a therapeutic antibody. In another embodiment, the antibody is a diagnostic antibody. In another embodiment, the antibody has a known utility selected from a therapeutic utility and a diagnostic utility.

In another embodiment, the present invention provides a multi-well container comprising 2 or more wells, each of which is labeled with a specific pair of labeled tRNA sets. "tRNA set," in this embodiment, refers to all tRNA associated with a particular amino acid in a cell to be tested. In another embodiment, the present invention provides a multi-well container comprising 3 or more wells, each of which is labeled with a pair of labeled tRNA sets. In another embodiment, the present invention provides a multi-well container comprising 5 or more wells, each of which is labeled with a pair of labeled tRNA sets.

In another embodiment, the present invention provides a multi-well container comprising 10 or more wells, each of which is labeled with a pair of labeled tRNA sets. In another embodiment, the present invention provides a multi-well container comprising 20 or more wells, each of which is labeled with a pair of labeled tRNA sets. In another embodiment, the present invention provides a multi-well container comprising 50 or more wells, each of which is labeled with a pair of labeled tRNA sets. In another embodiment, the present invention provides a multi-well container comprising 100 or more wells, each of which is labeled with a pair of labeled tRNA sets. In another embodiment, the present invention provides a multi-well container comprising 150 or more wells, each of which is labeled with a pair of labeled tRNA sets. In another embodiment, the present invention provides a multi-well container comprising 200 or more wells, each of which is labeled with a pair of labeled tRNA sets. In another embodiment, the present invention provides a multi-well container comprising 210 wells, each of which is labeled with a pair of labeled tRNA sets.

In another embodiment, the present invention provides the use of a multi-well container of the present invention to measure translation of a protein of interest. In another embodiment, the present invention provides use of a multi-well container of the present invention to characterize the translational profile of a cell of interest. In another embodiment, the multi-well container is designed for cells to be characterized and transfection agents to be introduced to each well, followed by assessment of translation according to a method of the present invention. Each possibility represents a separate embodiment of the present invention.

In another embodiment, the present invention provides a multi-well container comprising 2 or more wells, each of which is labeled with a pair of labeled tRNAs. In another embodiment, the present invention provides a multi-well container labeled with 3 or more pairs of labeled tRNAs. In another embodiment, the present invention provides a multi-well container labeled with 5 or more pairs of labeled tRNAs. In another embodiment, the present invention provides a multi-well container labeled with 10 or more pairs of labeled tRNAs. In another embodiment, the present invention provides a multi-well container labeled with 20 or more pairs of labeled tRNAs. In another embodiment, the present invention provides a multi-well container labeled with 50 or more pairs of labeled tRNAs. In another embodiment, the present invention provides a multi-well container labeled with 100 or more pairs of labeled tRNAs. In another embodiment, the present invention provides a multi-well container labeled with 150 or more pairs of labeled tRNAs. In another embodiment, the present invention provides a multi-well container labeled with 200 or more pairs of labeled tRNAs. In another embodiment, the present invention provides a multi-well container labeled with 300 or more pairs of labeled tRNAs. In another embodiment, the present invention provides a multi-well container labeled with 400 or more pairs of labeled tRNAs. In another embodiment, the present invention provides a multi-well container labeled with 500 or more pairs of labeled tRNAs. In another embodiment, the present invention provides a multi-well container labeled with 600 or more pairs of labeled tRNAs. In another embodiment, the present invention provides a multi-well container labeled with 700 or more pairs of labeled tRNAs. In another embodiment, the present invention provides a multi-well container labeled with 800 or more pairs of labeled tRNAs. In another embodiment, the present invention provides a multi-well container labeled with 900 or more pairs of labeled tRNAs. In another embodiment, the present invention provides a multi-well container labeled with all 990 pairs of labeled tRNAs. In another embodiment, the present invention provides the use of a multi-well container of the present invention to measure translation of a protein of interest. In another embodiment, the present invention provides use of a multi-well container of the present invention to characterize the translational profile of a cell of interest. In another embodiment, the multi-well container is designed for cells to be characterized and transfection agents to be introduced to each well, followed by assessment of translation according to a method of the present invention. Each possibility represents a separate embodiment of the present invention.

In another embodiment, once electromagnetic radiation of the required wavelength and energy has been administered to the biological sample, thereby exciting the donor fluorophores, an optical apparatus monitors fluorescence emanating from the cellular translation system. The acceptor fluorophores on the tRNA respond to this energy with the FRET signal whenever a donor and acceptor pair are in sufficient proximity, indicative of particular steps of translation activity.

Fluorescent radiation emitted from acceptor fluorophores is detected by the optical apparatus and the event is recorded by an image acquisition device.

In another embodiment, an acceptor fluorophore of the present invention emits a signal that is detectable through a means of detecting electromagnetic radiation "Detectable" as used herein refers to a signal able to be detected, over the background level, by standard means of detecting electromagnetic radiation. Means of detecting electromagnetic radiation are well known in the art. In some preferred embodiments, the signal is detected using total internal reflection fluorescence microscopy (TIR-FM) "TIR-FM" as used herein refers to a microscopy illumination method that illuminates a very small volume at the interface of two materials with different refractive indices. TIR-FM is described in WO 05/116252 and in US patent applications 2004/0023256 and 2006/0228708, which are incorporated herein in their entirety by reference.

Another microscopy method uses Low Angle Oblique (LAO) illumination for detecting optical signals deeper within cells, as described in Sako Y, Yanagida T (2003) Single-molecule visualization in cell biology. Nat Rev Mol Cell Biol 4 (Suppl): SS1-SS5

Additional means of detecting electromagnetic radiation include image acquisition devices; confocal laser scanning microscopes (LSM), used to improve fluorescence image quality by eliminating out-of-focus fluorescence; and spinning disk confocal microscopes, which can include video rate (typically 30 frames per second) imaging with charge-coupled device (CCD) cameras and imaging of 3-dimensional structures in living cells on a sub-second time scale with reduced photobleaching/phototoxicity (Graf et al, Live cell spinning disk microscopy. Adv. Biochem. Eng. Biotechnol. 95: 57-75, 2005). Programmable array microscopes (Hanley et al, An optical sectioning programmable array microscope implemented with a digital micromirror device, J Microsc 196: 317-331, 1999) and line scanning microscopes are available and offer similar advantages to spinning-disk confocals. In addition, multi-photon microscopes use infrared light, which readily penetrates up to 600 μM, allowing deep tissue imaging in living animals (Helmchen and Denk, Deep tissue two-photon microscopy. Nat Methods 2: 932-940, 2005). Additional methods are described inter alia in WO 2007/002758, WO 2008/028298, European Patent EP1428016, and U.S. Pat. No. 7,015,486 and US Patent application 2005/0157294, which are incorporated herein by reference. Each method represents a separate embodiment of the present invention.

According to one embodiment, the translation apparatus is placed in a test-tube and manually observed. In another embodiment, the system is placed in a multi-well plate such as a 96 or 384 well plate and observed by a high-throughput fluorimetry instrument.

According to another embodiment, the translation apparatus is placed under a microscope suitable for observing fluorescence at subcellular resolution, such as instruments available from Zeiss (Oberkochen, Germany) and Leica (Wetzlar, Germany), with an image acquisition device operable at a sufficient rate (10-100 frames per second) and computational units that can acquire and analyze the resulting images and data.

Assessing cellular translation activity can be accomplished in a variety of ways according to methods of the present invention. In one embodiment, a well of a 96-well plate or other commercially available multi-well plate is used to contain the biological sample. In another embodiment, the receptacle is the reaction vessel of a FACS machine. Other receptacles useful in the present invention include, but are not limited to 384-well plates. Still other receptacles useful in the present invention will be apparent to the skilled artisan to facilitate rapid high-throughput screening.

Overview of One Exemplary Embodiment of the Present Invention

A tRNA or a plurality thereof is engineered to carry a donor fluorophore and utilized as a donor, and a different tRNA or a plurality thereof is engineered to carry an acceptor fluorophore and utilized as an acceptor. The labeled tRNA are introduced into cultured cells or subcellular compartments. In order to monitor translation, a light source illuminates the cells, thus exciting the donor fluorophores and thereby the acceptor fluorophores whenever these components are in sufficient proximity to each other, generating a measurable signal.

If the labeled FRET pair, during the process of translation, is brought into close proximity, (often this distance is around 5 nm), a FRET signal is observed. When they are separated, the signal ceases. Since the distance in the ribosomes between A-Site and P-Site is about 35 Angstroms, and between the P-Site and E-Site is between 17-60 Angstroms (see Agrawal et al, Visualization of tRNA Movements on the *Escherichia coli* 70s Ribosome during the Elongation Cycle, J. Cell Biol. 2000 August 7' 150(3):447-460) and since the duration time of tRNA immobilization in the eukaryotic ribosome is around 0.5 second, a strong FRET signal is generated. Thus, generation of FRET signals from this pair indicates translation activity. The measurement can be the intensity of the signal or any other relevant feature, such as signal variability, signal polarity, signal lifetime, wavelength, photon number, spectrum, etc. as will be appreciated by one skilled in the art of fluorescent labeling and measurements.

One exemplary measurement measures the variability of the emitted signal. From this variability, it is possible to deduce the number of on/off events in the sample being measured. This is similar to measurements performed in Fluorescent Correlation Spectroscopy (FCS). In these applications, signal variation is measured and used for computing basic parameters of the system, such as the number of fluorescing molecules in the system. In FCS, the variability is mainly a function of molecules entering and leaving the illuminated volume. In an exemplary embodiment of the present invention, the variation is mainly caused by "blinking" (turning on and off) of the signals in response to protein translation activity. Thus, the translation activity being detected is evaluated from the ratio of variation to average signal intensity. Consequently, a signal that does not vary, e.g., in the event that the signal is constantly ON, is interpreted as lack of translation activity.

To compute the number of events, a person skilled in the art can use any suitable method known in the art, including, but not limited to, a method where the signal is measured over a period of time (preferably measured in seconds), and the autocorrelation is computed as follows:

$$N \sim \frac{EI_t^2}{\sum \delta I_t^2}$$

where $I_t$ is the signal strength at time t, and $\delta I_N$ is the signal deviation at time t (signal−average signal). In this way of measuring signal variations (with the accepted assumption that blinking follows a Poisson/Gaussian distribution), an estimate can be obtained on the event rate in the observed volume.

Introduction of tRNA and Nucleic Acid Molecules into a Target Cell

According to one embodiment of the present invention, labeled tRNAs are introduced into intact cells. This can be accomplished through a variety of established methods such as encapsulation of tRNA into liposomes or vesicles which are capable of fusion with cells. Fusion introduces the liposome or vesicle interior solution containing the tRNA into the cell. Alternatively, some cells will actively incorporate liposomes into their interior cytoplasm through endocytosis. The labeled tRNAs can also be introduced through the process of cationic detergent mediated lipofection (Feigner et al., Proc. Natl. Acad. Sci. USA 84:7413-17, 1987), or injected into large cells such as oocytes.

Additional methods for introduction of tRNA into a target cell are well known in the art. Such methods include the use of RNAiFect™ from Qiagen of Valencia, Calif. (Sako et al ibid) and electroporation. Sako et al discloses transfection of tRNA molecules, engineered to carry an anticodon for one of the natural stop codons (CUA, UUA, UCA) into A549 cells using the transfection agent RNAiFect (Qiagen, Hilden, Germany) is shown. The engineered tRNA were properly transfected and proved functional in a luciferase assay, where the luciferase gene included stop codons UGA, UAA, or UAG in place of the native Ser170 codon.

In another embodiment, INTERFERin™ (Autogen Bioclear™, Wiltshire, UK) is used for tRNA transfection. INTERFERin™ has been successfully used for tRNA transfection Additional methods for the introduction of nucleic acid molecules are described in Akhtar et al., (Trends Cell Bio. 2, 139, 1992). WO 94/02595 describes general methods for introduction of enzymatic RNA molecules. These protocols can be utilized for the introduction of virtually any nucleic acid molecule. Nucleic acid molecules can be administered to cells by a variety of methods known to those familiar to the art, including, but not restricted to, encapsulation in liposomes (WO03057164, Malone, R. W. et al., 1989, Proc. Natl. Acad. Sci. USA. 86: 6077-6081; Glenn, J. S. et al., 1993, Methods Enzymol. 221: 327-339; Lu, D. et al., 1994, Cancer Gene Ther. 1: 245-252), by microinjection (Liu et al., 2005, Dev Growth Differ. 47(5):323-31), by iontophoresis (Sakamoto et al., 2004, Gene Ther. 11(3):317-24), or by incorporation into other vehicles, such as hydrogels, cyclodextrins, biodegradable nanocapsules, and bioadhesive microspheres.

U.S. Patent Application No. 2004/235175 discloses a method of inserting RNA into cells. In this method, cells are transfected with RNA using electroporation in order to achieve high transfection efficiency.

In another, non-limiting exemplary electroporation protocol, 3-40×$10^6$ cells, preferably growing at log phase, are harvested, counted and washed with cold 1× HeBS (Hepes-buffered saline). Cells are resuspended in 0.8 mL 1× HeBS containing the tRNA and incubated at room temperature for 15 minutes. An exemplary recipe for HeBS is 20 mM HEPES, 150 mM NaCl, pH 7.0-7.4. The tRNA/cell suspension is transferred to an electroporation cuvette and electroporated at an appropriate voltage, preferably at between 500-2000 μF capacitance. The time constant is recorded if desired, and the mixture is optionally incubated in the cuvette for about 10 minutes at room temperature, prior to returning the cells to culture media.

In another, non-limiting exemplary electroporation protocol successfully used for CHO-K1 cells, HEK cells, and rat hippocampal neurons (thus having utility for a large variety of cell types), tRNA is precipitated (either alone or as a coprecipitate with DNA) in ethanol and ammonium acetate at −20° C. for at least 1 hour. The precipitated tRNA is pelleted, vacuum dried, and resuspended in $CO_2$-independent medium to the desired final concentration (4 μg/μl tRNA, either with our without 2.5 μg/μl carrier DNA, is typically appropriate). Immediately prior to electroporation, the media is replaced with $CO_2$-independent media, containing no glutamine, FBS or antibiotics. $CO_2$-independent media are available e.g. from Invitrogen-Gibco and include phenol red free media, Liebovitz's L15 Media (catalogue no. 11415-114), and catalogue nos. 18055-088; 18045-088, and 041-95180M. Approximately 5 μl of electroporation solution is added to the cells, followed by electrical pulse application. For CHO-K1 cells and HEK cells, four 120 V pulses of 50 ms duration are typically used, and for neurons, four 160 V pulses of 25 ms duration. The $CO_2$-independent media is immediately replaced with fresh Ham's F12 media for CHOK1 cells; DMEM for HEK cells, or neurobasal media for neurons, and cells are returned to the 37° C. incubator.

In another, non-limiting exemplary electroporation protocol, electrolyte-filled fused silica capillaries (30 cm long, 30-μm id., 375-μm od) are used. The outlet end of the capillaries is tapered to an approximate outer tip diameter (typically 50 μm, depending on the size of the cell type used). Exemplary electrolytes useful in this method are those based on HEPES buffer. The tapered outlet end of the capillary is submerged in the buffer contained in the cell chamber, and the inlet end is placed in a buffer-filled vial. Both the capillary and the inlet vial buffer solutions contain the tRNA and/or any other components to be transfected. Cells are placed in a chamber on the microscope stage, and cell bathing medium (HEPES buffer) is electrically grounded. The capillary outlet is placed within 5 μm of the cell surface, and the DC high voltage power supply is connected.

In another, non-limiting exemplary electroporation protocol, cells are electroporated using a modified patch-clamp technique. Single cells under direct observation are indented with a microelectrode and electroporated using a current delivered from a simple voltage-clamp circuit, as described in detail in Rae J L and Levis R A, Single-cell electroporation, Pflugers Arch 443(4):664-70, 2002.

Figure 3:
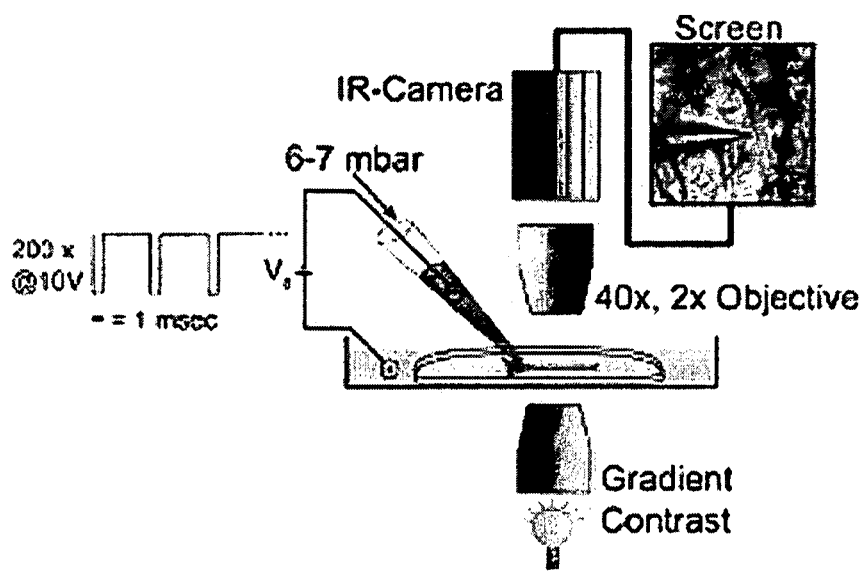
FIG. 3 is an illustration of a modified standard electrophysiology setup used for electroporation-mediated transfection. The culture is placed in a perfusion chamber and visualized using gradient-contrast illumination and IR video microscopy with a 40× water immersion objective and further 2× magnification. Individual neurons can be identified on the monitor screen. The DNA filled micropipette can be targeted precisely to the membrane of a single soma. A back-pressure of 6-7 mbar is applied to the pipette. Two hundred 1 ms-long square pulses with an interpulse delay of 4 ms and an amplitude of 10 V are delivered to each neuron.
Figure 4:
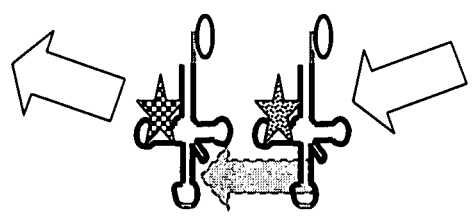
FIG. 4 is a schematic presentation of tRNA-tRNA FRET. An exemplary method of attaching a fluorophore to tRNA is depicted. Stars denote fluorescent labels on the D-loop of each tRNA. Arrows (from right to left) denote excitation of the donor, energy transfer to acceptor (dotted gray arrow), and emission from the acceptor, respectively.

In another, non-limiting exemplary electroporation protocol successfully used for electroporation of DNA, but equally useful for tRNA, into individual neurons in cultures of organotypic brain slices (FIG. 3), micropipettes with a tip diameter of about 1-2 μm and with resistances of 10-20 MΩ are pulled from capillary glass with filament (available from Science Products, Hofheim, Germany, catalogue number GB150E-8P) on a Micropipette Puller (available from Sutter Instrument Company, Novato, USA catalogue number P-97). Micropipettes are mounted on a three-axis micromanipulator (Luigs and Neumann, Ratingen, Germany). A Millicell CM insert (Millipore, Billerica, Mass., USA) containing a brain slice is placed in a perfusion chamber on the stage of a Zeiss Axioplan™ microscope and continuously perfused with oxygenated physiological salt solution during electroporation. The overall time under perfusion is typically about 30 min. Slices are transferred back into the incubator, individual cell somata are identified, and a pipette tip is gently placed against the cell membrane. Voltage pulses are delivered between an electrode placed inside the micropipette in contact with the tRNA solution (cathode), and a ground electrode (anode) using an isolated voltage stimulator (available from WPI, Berlin, Germany, under the name HI-MED HG-203) controlled by a tetanizer (available from Sigmann Elektronik, Hueffenbart, Germany). To prevent the tip from clogging and dilution of the tRNA, a back-pressure (typically 2-10 mbar) is applied to the pipette. In an exemplary embodiment, a single train of 200 square pulses with a duration of 1 ms is applied, using a 4 ms delay with an amplitude of 10 V. The 1 ms pulses remove the negatively charged tRNA from the pipette by electrophoresis, driving electroporation. Typically, no voltage is applied during the delay of 4 ms between the pulses and thus there is no current flowing through the circuit.

Each method for introduction of tRNA into a cell represents a separate embodiment of the present invention.

Introduction of tRNA into Subcellular Compartments

Vestweber and Schatz (Nature 338: 170-172, 1989) achieved uptake of both single- and double-stranded oligonucleotides into yeast mitochondria by coupling the 5' end of the oligonucleotide to a precursor protein consisting of the yeast cytochrome c oxidase subunit. Seibel et al. (Nucleic Acids Research 23: 10-17, 1995) have described the import into the mitochondrial matrix of double-stranded DNA molecules conjugated to the amino-terminal leader peptide of the rat ornithine-transcarbamylase.

Methods for the introduction of nucleic acid molecules into the interior of an organelle are disclosed in WO2003/052067. WO2005/001062 discloses the use of viral vectors that contain localization signals specific for the target organelle. These protocols can be utilized for the introduction of labeled tRNAs into a mitochondria or chloroplast.

Labeling and Detection According to the Present Invention

In other embodiments, methods of the invention can be carried out in accordance with the following alternatives:

tRNA labeling. Methods for fluorophore labeling of tRNA (FIG. 1) are well known in the art and are described inter alia in U.S. Pat. No. 7,288,372 and U.S. Patent applications 2003/0219780 and 2003/0092031, which are incorporated herein by reference.

In another exemplary method, used for Met-tRNA (Jun S Y et al, Fluorescent labeling of cell-free synthesized proteins with fluorophore-conjugated methionylated tRNA derived from in vitro transcribed tRNA. J Microbiol Methods. 2008 June; 73(3):247-51) but suitable for any tRNA, 10 µl of 30 mM succinimidyl ester of fluorescent dye in dimethy sulfoxide (DMSO) is added to 40 µl of the Met-tRNAfMet-resuspended solution and incubated for 40 min on ice. The reaction is stopped by adding one-tenth volume of 2M sodium acetate, pH 5.0. Fluorophore-conjugated Met-tRNAfMet is extracted repeatedly with an equal volume of acid phenol:chloroform (1:1, v/v; pH 5.0. Two and a half volumes of cold 95% (v/v) ethanol solution are added to the aqueous phase, and the mixture is allowed to stand at −70° C. for 1 h to precipitate fluorophore-conjugated Met-tRNAfMet. The precipitated pellet is collected by micro-centrifugation at 14,000 rpm at 4° C. for 20 min, and then resuspended in an equal volume of diethyl pyrocarbonate (DEPC)-treated water to the original reaction volume. After alcohol precipitation, the precipitate is washed with 80% (v/v) ethanol solution, dried under vacuum, and resuspended in 20 µl of DEPC-treated water.

In another exemplary method, used for conjugation of BODIPY-FL to Met-tRNA (Olejnik J et al, N-terminal labeling of proteins using initiator tRNA. Methods. 2005 July; 36(3):252-60), but suitable for conjugation of BODIPY-FL to any tRNA, 1.0 OD$_{260}$ (1500 pmol) of methionyl-tRNAfMet (tRNAfMet [Sigma Chemicals, St. Louis, Mo.], aminoacylated with methionine) is dissolved in water (37.5 µl), followed by addition of 2.5 µl of 1N NaHCO$_3$ (final conc. 50 mM, pH 8.5), followed by 10 µl of 10 mM BODIPYFL-SSE solution (Molecular Probes, Eugene, Oreg.). The modification reaction is allowed to proceed for 10 min at 0° C. and quenched by the addition of 0.1 volume of 1M lysine. 0.1 volume of 3M NaOAc, pH 5.0, is added, and modified tRNA is precipitated with 3 volumes of ethanol, dissolved in 50 □l of water, and purified on a NAP-5 column (Amersham-Pharmacia, Piscataway, N.J.) to remove any free fluorescent reagent.

In general, tRNA molecules can be tagged while retaining their interaction with the aminoacyl synthetases as well as retaining their functionality with the ribosome. tRNAs have been tagged with fluorescein (Watson et al., 1995, Biochemistry. 34 (24): 7904-12), with tetra methyl rhodamine (TMR) (Jia et al., 1997, Proc Natl Acad Sci USA. 7932-6), and with proflavine and ethidium bromide (Wintermeyer and Zachau, 1971, FEBS Lett. 18 (2): 214-218). In another embodiment, the fluorophore is selected from the group consisting of fluorescein, rhodamine, proflavine and ethidium bromide.

Certain preferred embodiments of the present invention include labeling the tRNA with small organic dyes attached to the "shoulder" region of the tRNA, such as in positions 8 and 47 of E. coli tRNAs, which have been often used for this purpose. One particular labeling method is attaching the label of choice to one or both of the dihydrouridines in the D-Loop of the tRNA. Most tRNA have these dihydrouridine modifications, enabling a wide choice of labels, including rhodamines, which are very useful due to their low tendency to bleach and high signal strength. The most widely used dyes are FITC and (excitation and emission peaks at 490 nm and 520 nm) and TMR (excitation peaks at 550 nm and emission at 573 nm).

Typically, FRET occurs only when neighboring sites in the ribosome (for example A and P, or P and E) are occupied by a donor-acceptor pair. For example, if 10% of all cellular tRNA is labeled, then on average approximately 1% of active ribosomes will be in a FRET configuration (0.25% in each of PA, AP, PE, EP configurations, wherein A,P,E indicate the ribosomal tRNA sites, and donor is in the first and acceptor in the second site).

According to another embodiment of the present invention, the ratio of immobilized tRNAs in adjacent ribosomal sites is detected by measurement of FRET resulting from interaction between donor and acceptor fluorophores attached to the corresponding tRNAs. When both the donor and the acceptor fluorophores are attached to one or more species of the tRNAs, an elongation activity is detected.

In certain preferred embodiments, fluorophores utilized in the present invention exhibit a high quantum yield of fluorescence at a wavelength different from native cell components; e.g. nucleic acids and amino acids. Upon excitation at a preselected wavelength, the marker is detectable at low concentrations either visually or using conventional fluorescence detection methods.

Systems and Methods for Study of Translation in Subcellular Compartments and Uses Thereof.

Methods of the present invention enable monitoring of translation of selected transcripts of interest in various specific subcellular compartments such as mitochondria, chloroplasts, and dendritic spines. In mitochondria and chloroplasts, the entire translation apparatus, including ribosomes, ribosomal proteins, translation factors, tRNAs and the genetic code, are specific to the subcellular compartment and distinct from those of the host eukaryotic cell. Also, apart from the ribosomal RNA and tRNA, other proteins of the translation apparatus are synthesized in the cell cytoplasm and imported into the subcellular compartment. This allows a specific assay to be developed, wherein the tRNA of choice are labeled in the cell. In another embodiment, the tRNA are labeled in an isolated subcellular compartment. In both cases, the labeled tRNA are directed to and imported into the subcellular compartment. Thus the measured signals pertain to subcellular compartment only and not to the general cellular translation apparatus.

Host Cells

Any cell is suitable for assaying translation by methods of the present invention. Non-limiting examples of target cell types are COS, HEK-293, BHK, CHO, TM4, CVI, VERO-76, HELA, MDCK, BRL 3A, NIH/3T3 cells, etc. Additional cell lines are well known to those of ordinary skill in the art, and a wide variety of suitable cell lines are available from the American Type Culture Collection, 10801 University Boulevard, Manassas, Va. 20110-2209. Cells of particular interest include neuronal cells, immune system cells, including lymphocytes (B and T cells e.g., T helper cells) and leucocytes (e.g., granulocytes, lymphocytes, macrophage and monocytes), cells from lymph, spleen and bone marrow tissues, epithelial cells, and cells from or derived from internal organs.

Signal Detection

The signals emitted by the cells or organelles of the present invention can be detected by a variety of different instrument configurations. As a bulk assay, they can potentially be read manually, by comparing the fluorescent signal to calibrated standards under a fluorescent reader. Alternatively, they can be read by a fluorescent plate reader, made for 96-well plates, 384-well plates, or another configuration known in the art. In another embodiment, the labeled cells are imaged by a microscope, to identify subcellular localization of protein synthesis processes and to estimate the relative rates of protein synthesis in various regions of the cell. In further embodiments, instruments capable of single-molecule detection in living cells are used.

Signal Analysis

There are numerous methods to process and analyze the resulting signals. In one embodiment, donor, acceptor and FRET signals are separately measured and compared to yield the fraction of pairs in FRET position versus the total concentration of donors and acceptors separately. When repeating such measurements with various concentrations of labeled components vs. unlabeled samples, it is possible to derive the overall fraction of component pairs versus the total number of components. For example, if 10% of tRNA are labeled as donors and 10% as acceptors, then about 4% of ribosomes will include a FRET tRNA pair in neighboring ribosomal positions (1% AP, 1% PA, 1% PE, 1% EP, where donor is always first and acceptor second). This creates a specific ratio of donor/acceptor/FRET signals. If only 5% are labeled as donors or acceptors, than only 1% FRET signal will occur. Thus the FRET signal strength is proportional to the square of the donor/acceptor signals. This allows a calibration curve to be derived, for example in cell-free system, and later used in living cells to provide a precise estimate of the relative concentration of components in FRET position as well as the concentration of all components.

In another embodiment, signal variance is computed, and the square of the ratio of average signal to average variance is computed, which yields an estimation of the number of labeled components being measured. This assumes that the process underlying this variation is of Poissonian or Gaussian nature, such as in molecules diffusing into and out of a certain volume, or the blinking of labeled ribosomes in response to protein synthesis. When considering a sizable number of ribosomes (10 or more), the process can be assumed to be governed by Poissonian or Gaussian statistics, depending on the number. In such cases, as is well known, the variability of the signal is proportional to the square root of the signal strength. For example, let the measured signal be denoted by $S_t$, and let its average over a period of time (for example a few seconds) be denoted by $S_{av}$. The variance $Var(S)$=average $(S_t-S_{av})$. In such processes, the size of the variance is on average the square root of the signal. Thus $Var(S) \sim sqrt(S_{av})$= sqrt(NS) where S is the signal from a single event (for example FRET from a pair of labeled components). This means that $(S/Var(S))^2$=NS/S=N or the number of active particles.

Application of the Present Invention for Diagnostic Applications

The methods disclosed herein are suitable for diagnostic applications, wherein rates of protein synthesis are indicative of type or phase of a disease or condition. For the purpose of diagnosis, cells are obtained from the host, for example, from biopsy, and prepared for the assay. In another embodiment, the preparation comprises the following steps:

(a) introducing the labeled tRNA into the cells by means of transfection; and (b) detecting radiation emitted from the cells.

In another embodiment, the method further comprises the step of analyzing the radiation or a signal derived thereof, thereby obtaining a readout of translation activity.

Prior to detection, cells are commonly transferred to a carrier. The type of carrier depends on the type of measurement that is used for detection. Thus, a carrier includes, but is not limited to, a fluorescent plate reader.

In another embodiment, the above method is applied in a high-throughput operation. In another embodiment, the method is applicable for accurate measurements of subcellular localization of protein synthesis events, for example, detection of translation activity in mitochondria or neuronal spines.

According to some embodiments, the method further comprises comparing the amount of detected radiation to a reference standard, wherein a level of detected radiation different from the reference standard is indicative of a particular disease or disorder. In another embodiment, the level of detected radiation is diagnostic for a disease, disorder or pathological condition. In other embodiments, the readout provided upon analysis of the detected electromagnetic radiation is indicative of or diagnostic for a disease, disorder or pathological condition.

Pathological conditions that are amenable to diagnosis using methods of the invention include without limitation, fragile X mental retardation, autism, aging and memory degeneration.

Diseases that are amenable to diagnosis using methods of the invention include without limitation, mitochondria-related disease, cardiac hypertrophy, restenosis, diabetes, obesity, a genetic disease resulting from a premature termination codon (PTC), and inflammatory bowel disease.

Other conditions that are amenable to diagnosis using methods of the invention include malignant and pre-malignant conditions. Malignant and pre-malignant conditions include those which occur in hematological cells, such as a hematological malignancy. Hematological malignancies include without limitation, acute lymphoblastic leukemia (ALL); acute myelogenous leukemia (AML); chronic myelogenous leukemia (CML); Hodgkin's disease; non-Hodgkin lymphoma; chronic lymphocytic leukemia (CLL); diffuse large B-cell lymphoma (DLBCL); follicular lymphoma (FL); mantle cell lymphoma (MCL); hairy cell leukemia (HCL); marginal zone lymphoma (MZL); Burkitt's lymphoma (BL); post-transplant lymphoproliferative disorder (PTLD); T-cell prolymphocytic leukemia (T-PLL); B-cell prolymphocytic leukemia (B-PLL); Waldenstrom's macroglobulinemia and multiple myeloma (MM). In one embodiment, the malignant disorder is multiple myeloma.

Pre-malignant conditions include without limitation, monoclonal gammopathy of uncertain significance and smoldering multiple myeloma.

Application of the Present Invention for High-Throughput Screening (HTS) Assays

The methods disclosed herein can optionally be used for the screening of a large library of small molecules, recombinant proteins, peptides, antibodies, or other compounds to determine their efficacy or their potential for use as drugs, based on measuring the effect of a test compound on translation of a specified protein in a test cell. High-throughput screening utilizes an assay that is compatible with the screening instrument, enables quick rejection of most of the compounds as irrelevant, and approves only a small fraction for continued research. The present invention is suitable for very thorough and informative HTS assays, in the sense that it provides real-time measurement of translation of specified proteins in viable cells.

Thus, functional activity of a compound on a specific cell type can be usefully studied by subjecting it to a translation monitoring assay of the present invention. A cell line with tagged tRNA is cultured and placed in a multi-well plate. This can have a 96-well plate format, a 384-well plate format or any other format compatible with automated screening. The wells in the plate need to be optically amenable for detection.

A robot administers one compound from the library into each well, and signal detection is performed. A suitable sampling regime should be adopted. As an illustrative example, a measurement can be taken for 30 seconds every 10 minutes for a total of one hour. Other regimes can optionally be also used. The effect of the compound on translation activity can thus be detected.

It is understood by the skilled artisan that while various options (of compounds, properties selected or order of steps) are provided herein, the options are also each provided individually, and can each be individually segregated from the other options provided herein. Moreover, steps which are obvious and known in the art that will increase the sensitivity of the assay are intended to be within the scope of this invention. For example, there may be additional washing steps, blocking steps, etc. It is understood that the exemplary embodiments provided herein in no way serve to limit the true scope of this invention, but rather are presented for illustrative purposes. All references cited herein are expressly incorporated by reference in their entirety.

The following examples are presented in order to more fully illustrate some embodiments of the invention. They should, in no way be construed, however, as limiting the broad scope of the invention.

EXAMPLES

Example 1

Labeling Two Parts of the Translational Machinery as a Fret Pair

Two different tRNA molecules are labeled as a FRET pair. For example, some tRNAs (FIG. 1) can be labeled with a donor fluorophore, and others with a corresponding acceptor fluorophore such as Cy3 (excitation and emission peaks are 550 and 570 nm, respectively) and Cy5 (excitation and emission peaks are 650 and 670 nm, respectively); when translation is active, such tRNAs are immobilized in two adjacent sites (A and P or P and E) of the ribosome, thereby producing a FRET pair which produces measurable FRET signals. These signals indicate that the A and P sites are populated with labeled tRNAs. A small signal indicates that a low percentage of the A and P sites are populated, and therefore that the translation apparatus is in a state of low production rates. Additional exemplary, non-limiting FRET combinations are listed in Table 3.

TABLE 3

Exemplary FRET combinations.

| Donor fluorophore | Acceptor fluorophore |
|---|---|
| Cy3 | Cy5 |
| Rhoadmine 110 | Cy3 |
| Cy3 | Cy5.5 |

Three docked tRNAs are shown in FIG. 1. The first 32 is in the A (Aminoacyl) site; the second 33 in the P (Peptidyl) site, and the amino acid it carries is at this point connected to the nascent peptide; the third 34 is in the E (exit) site, it has been discharged from the amino acid and will be ejected shortly from the ribosome. The heavy line 30 indicates the mRNA being translated, and the dotted line 45 represents the polypeptide being synthesized, tied into the Peptidyl position.

The main stages of elongation are as follows. Stage 1: Codon recognition. A tRNA molecule carrying an amino acid binds to a vacant A-site, while the nascent polypeptide is attached to the P-site. Stage 2: Peptide bond creation. A new peptide bond is created and the polypeptide chain is moved to the A-site. Stage 3: Translocation. The ribosome translocates a distance of 3 nucleotides with respect to the mRNA, the two tRNA units and the polypeptide chain. Stage 4: the cycle repeats itself until a stop codon is reached.

Three types of tRNA are shown with respect to fluorescent labeling. The tRNAs 40 and 43 are unlabeled. tRNAs 33 and 42 (marked with vertical lines) are labeled as FRET donors. tRNAs 41 and 32 (marked with horizontal lines) are labeled as FRET acceptors. When freely diffusing (as in the case of 41 and b), the chance of a FRET pair forming for a measurable length of time is negligible. However, when a pair is immobilized on the ribosome (as in the case of 32 and 33), a FRET pair is formed for about 500 milliseconds (in eukaryotes), which is sufficient for detection.

The larger the number of active ribosomes, the larger the probability of juxtaposition of such pairs, and the larger the FRET signal. In addition, signal variability can be used to estimate the concentration of active ribosomes. Also, with a microscope, subcellular localization of protein synthesis can be quantitatively estimated. tRNA pairs that are not immobilized in such a way either diffuse in he cytoplasm or else are bound to non-labeled molecules such as translation factors or amino-acyl synthetases, and therefore do not create FRET pairs, yielding no measurable signal. This basic principle holds for any choice of FRET pairs.

Example 2

Introduction of the Labeled tRNAs into CHO Cells

Figure 2:
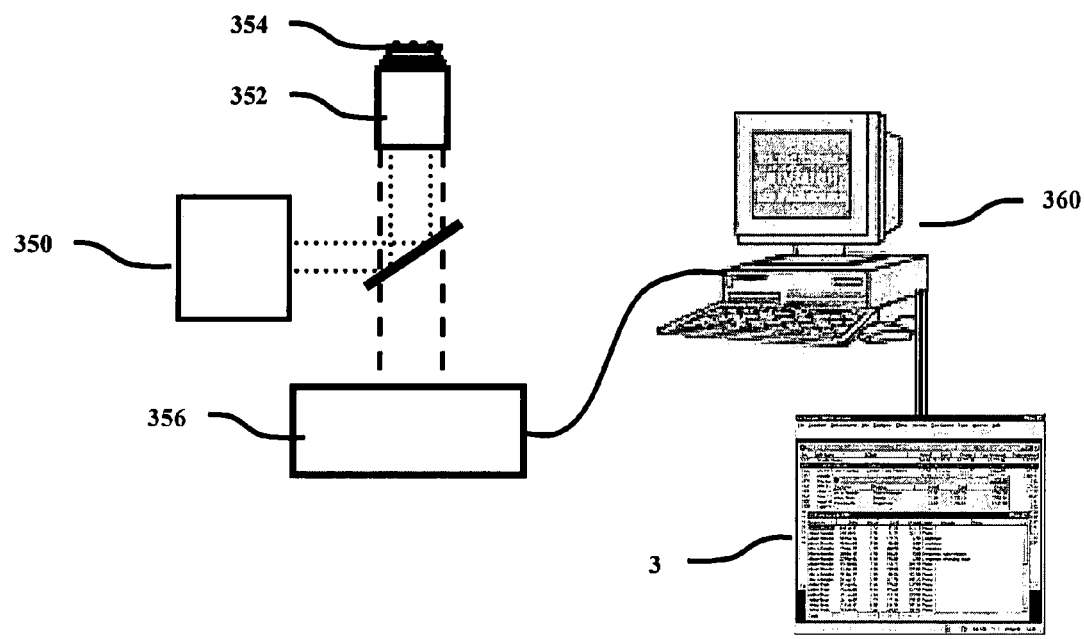
FIG. 2 is an exemplary overview of one preferred embodiment for signal generation and analysis. Illumination module 350 illuminates sample 354 through microscope 352, and the resulting signals are detected by detection module 356. The resultant image can then be transferred to computerized analysis station 360 which analyzes the images, preferably records the produced signals, and analyzes them to produce an estimation of the specific measurement that is required. The readout can be presented on the computer screen and if desired stored in database 362 for further analysis.

Labeled tRNAs are transfected into CHO cells using Trans-Messenger transfection reagent (Qiagen, Hilden, Germany) according to the manufacturer's protocol. Transfected cells are placed under a microscope equipped for single molecule detection (Zeiss, Oberkochen, Germany) with an image acquisition device operable at a sufficient rate (10-100 frames per second), and computational units that can acquire and analyze the resulting images and data (FIG. 2). Translation of the tRNA of interest is measured.

For high-throughput screening, transfected cells are cultured in a 96-well plate format, compatible with automated screening. A robot administers one compound out of the library being screened into each well and translation detection is performed. A suitable sampling regime is adopted. The effect of the compound on translation activity is detected in comparison with negative control signal.

Example 3

Diagnostic Applications

A selected yeast tRNA is labeled with donor fluorophore and stored. Another selected yeast tRNA is labeled with acceptor fluorophore and stored. Prior to the assay, two aliquots of donor- and acceptor-labeled tRNA are mixed. The mixture is transfected into the cells to be diagnosed, for example, by using the transfection kit RNAiFect™ (Qiagen, Hilden, Germany). The cells may be human cells, for example, human cells obtained from a tissue removed by biopsy. The transfected cells are introduced into a 96 well-plate. Signals are collected from the plates using a fluorescent plate reader and are subjected to computerized analysis/es. Typically, the parameters derived for the analysis are: average signal strength, average signal deviation, or percentage of labeled tRNA of a given species in each well. These parameters are monitored over time and in response to treatment. Values before and/or after treatment are compared to known standards to infer clinical parameters of the cells.

Example 4

Formation and Translocation of a Pre-Translocation (PRE) Complex

Three samples of PRE complex, containing $tRNA^{Met}$ in the ribosomal P-site and fMetPhe-$tRNA^{Phe}$ in the ribosomal A-site made with mRNA-fMetPheLys programmed ribosomes were formed in parallel, by addition of: i) both fMet-$tRNA^{fMet}$(Cy5) and Phe-$tRNA^{Phe}$(Cy3) (the donor-acceptor or DA sample); ii) unlabeled fMet-$tRNA^{fMet}$ and Phe-$tRNA^{Phe}$(Cy3) (the donor alone or DU sample); and iii) fMet-$tRNA^{fMet}$(Cy5) and unlabeled Phe-$tRNA^{Phe}$ (the acceptor alone or UA sample). These complexes, which result in fMet-Phe formation, were purified by ultracentrifugation through a sucrose cushion prior to their utilization in the fluorescence measurements described below. The stoichiometries of fMet-Phe formed, and of [$^3$H]-Phe and [$^{35}$S]-fMet cosedimenting with the ribosome in the PRE complexes, are very similar whether using Cy3-labeled or unlabeled Phe-$tRNA^{Phe}$ (DU and DA samples vs. UA sample) or Cy5-labeled or unlabeled fMet-$tRNA^{fMet}$ (UA and DA samples vs. DU sample). These results provide a convincing demonstration of the functionality of the Cy-labeled tRNAs in binding to the ribosome and participating in formation of a dipeptide, as part of PRE complex formation.

Figure 5A:
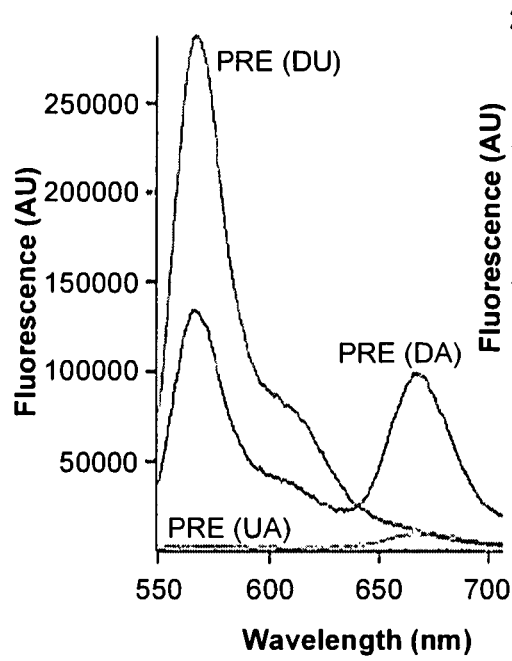
FIG. 5 shows the results of ensemble tRNA:tRNA FRET. Fluorescence spectra of PRE (FIG. 5A) and POST (FIG. 5B) complexes formed with the donor-acceptor (DA) [Phe-tRNA$^{Phe}$ (Cy3)+fMet-tRNA$^{fMet}$ (Cy5)]; the donor alone (DU) [Phe-tRNA$^{Phe}$ (Cy3)+unlabeled fMet-tRNA$^{fMet}$], and the acceptor alone (UA) [Phe-tRNA$^{Phe}$+fMet-tRNA$^{fMet}$ (Cy5)] samples. The upper and middle traces in each of FIGS. 5A and 5B are fluorescence intensities monitored at acceptor (680±10 nm) and donor (570±10 nm) wavelengths, respectively. The lower trace in each of FIGS. 5A and 5B measures the change in acceptor fluorescence in the presence of added viomycin.
Figure 5B:
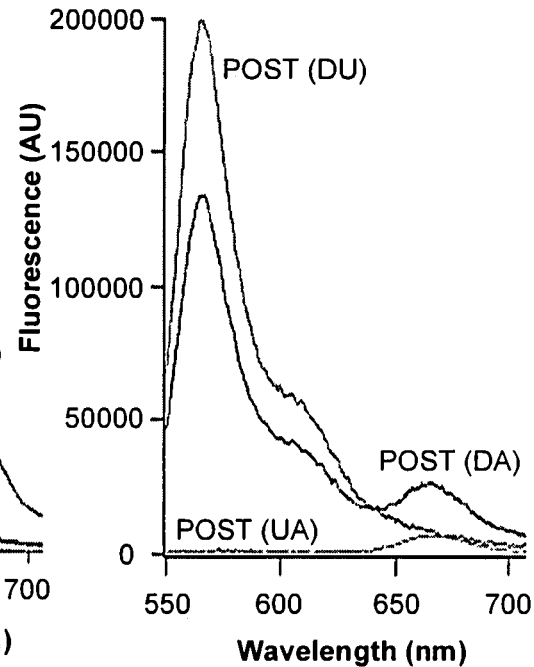

Fluorescence spectra of the three PRE samples (FIG. 5A) provide clear evidence of FRET in the DA sample, as shown by the increase in acceptor and decrease in donor fluorescent intensities relative to the A and D samples, respectively. Addition of EF-G•GTP to each of the samples leading to post-translocation (POST) complex formation results in a marked decrease in FRET efficiency, as evidenced by the decreases in the differences observed comparing the DA sample with both the UA and DU samples (FIG. 5B). This decrease in FRET efficiency is consistent with an increase in the distance between the dihydrouracil positions of $tRNA^{Phe}$ and $tRNA^{fMet}$ as these two tRNAs move from occupying the A- and P-positions, respectively, in the PRE complex, to occupying the P- and E-positions, respectively, in the POST complex.

Example 5

In-Vitro Protein Sequencing

Figure 6A:
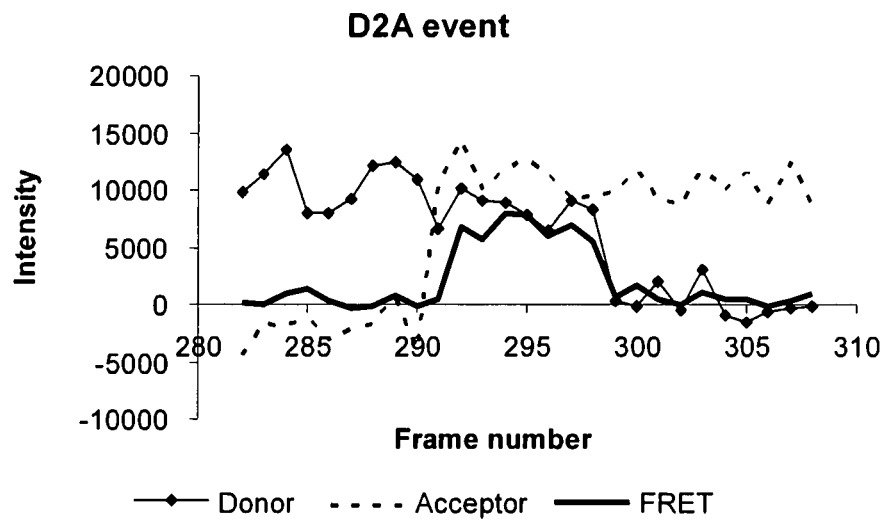
FIG. 6A shows events excised from traces of a ribosome translating an mRNA of sequence MRFVRFVRF (SEQ ID NO:10)
Figure 6B:
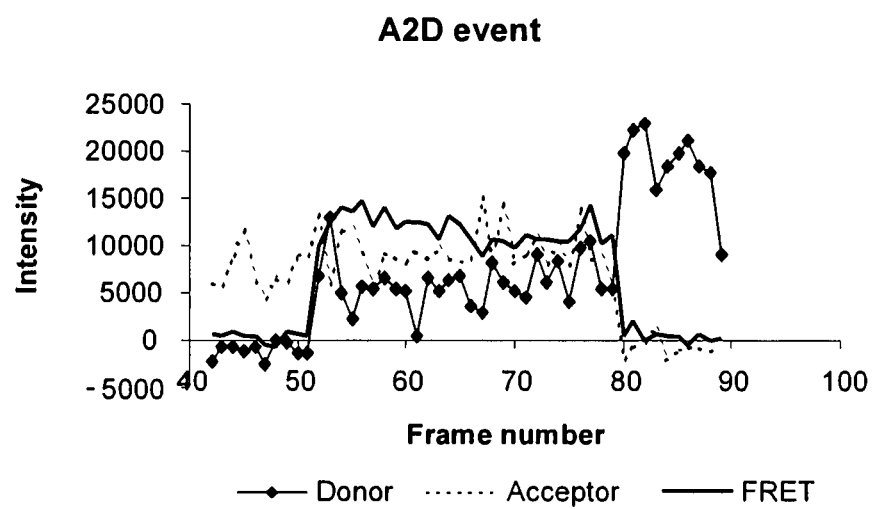
FIG. 6B shows events excised from traces of a ribosome translating an mRNA of sequence MFRVFRVFR (SEQ ID NO:11). The figures show events excised from traces of single ribosome experiments. For the experiment, tRNA$^{Arg}$ was labeled with Cy3 (donor) and tRNA$^{Phe}$ was labeled with Cy5 (acceptor). The traces show the donor emission under donor excitation (legend: donor), acceptor emission under acceptor excitation (legend: acceptor) and FRET, or sensitized emission, which is acceptor emission under donor excitation (legend: FRET).

In this experiment the dynamics of a single ribosome translating a known message in a cell-free system under a single-molecule detection system was followed. FIGS. 6A and 6B show events excised from traces of single ribosome experiments. The ribosome was translating the message MRFVR-FVRF (FIG. 6A) and MFRVFRVFR (FIG. 6B). $tRNA^{Arg}$ was labeled with Cy3 (donor) and $tRNA^{Phe}$ was labeled with Cy5 (acceptor). The traces show the donor emission under donor excitation (legend: donor), acceptor emission under acceptor excitation (legend: acceptor) and FRET, or sensitized emission, which is acceptor emission under donor excitation (legend: FRET).

In FIG. 6A, an event is shown where a $tRNA^{Phe}$ joins an incumbent tRNA(Arg). Acceptor and FRET traces increase instantaneously and simultaneously at frame 290 as the $tRNA^{Phe}$ binds; then donor and FRET disappear, again instantaneously and simultaneously at frame 298 as the $tRNA^{Arg}$ dissociates.

In FIG. 6B, an event is shown where a $tRNA^{Arg}$ joins an incumbent $tRNA^{Phe}$. Donor and FRET traces increase instantaneously and simultaneously at frame 45 as the $tRNA^{Arg}$ binds; then acceptor and FRET disappear at frame 80 as the $tRNA^{Phe}$ dissociates, simultaneously with increase of donor intensity due to dissociation of the FRET pair (leaving the entire energy with the donor).

Example 6

Live Cell tRNA:tRNA FRET Imaging

To demonstrate the feasibility of the assay system of the invention, bulk yeast tRNA labeled with rhodamine 110 as donor and with Cy3 as acceptor were used. Fluorescent labeled tRNA were then introduced into live HEK-293, HeLa and CHO cells, employing a transfection protocol. One day prior to the transfection experiment, the cells were seeded on fibronectin-coated glass slides in a 24-well plate. On the following day, the growth medium was removed and 0.5 ml of fresh medium was added to each well containing the sub-confluent monolayers. 10 minutes later, 0.1 ml of the labeled-tRNA mixed with the transfection reagent and serum-free media were added to each well. The plate was incubated at 37° C. in a 5% $CO_2$ incubator for 6-8 hr, followed by fixation with 4% paraformaldehyde for 20 min and mounting using fluorescent mounting medium. The fixed cells on glass slides were then visualized employing a spinning disk confocal microscope. Stable GFP expressing cells showed increased GFP fluorescence, indicating increased protein synthesis rates for 2-36 hours following transfection with tRNA.

In order to determine the imaging parameters to be employed in the following experiments, including the degree of non-specific signal stemming from the cross-stimulation of different fluorophores, cells were transfected with donor only and with acceptor only, and imaged in the exact conditions employed for the FRET measurement. The calibration coefficients for computing the NFret (corrected FRET) image were NFret=FRET−0.011*donor−0.004*acceptor. In addition to the basic identification of a true FRET signal, indicative of the proximity of the labeled tRNAs when immobilized in the ribosome, cycloheximide was utilized to freeze the dynamic process of the functionally important change in localization of the tRNAs. Imaging of the same cells prior to and following cycloheximide treatment, confirmed the expected increase in FRET signal intensity in both HEK and CHO cells. Furthermore, the signal obtained in CHO cells was markedly stronger than the one obtained in HEK cells under similar transfection and imaging conditions. This is an indication of the correlation of signal intensity with synthesis rates, as CHO cells are known to be strong protein producers.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method for measuring rate of translation of a protein of interest in a biological sample comprising:

(i) providing a biological sample comprising a protein of interest;

(ii) introducing into the biological sample at least one first tRNA FRET pair capable of reading at least one first codon pair occurring in the mRNA sequence encoding said protein of interest at a frequency that is at least five-fold higher than the general frequency of said at least one first codon pair in a reference proteome or transcriptome; wherein one tRNA member of the at least one tRNA pair is labeled with a donor fluorophore and the other tRNA member is labeled with an acceptor fluorophore; and (iii) detecting FRET signals emitted from the biological sample, thereby measuring rate of translation of the protein of interest.

2. The method according to claim 1, wherein said at least one first codon pair occurs in said mRNA sequence at a frequency that is at least ten-fold higher than the general frequency of said at least one first codon pair in a reference proteome or transcriptome.

3. The method according to claim 1, wherein said at least one first codon pair is having an enrichment factor of at least 6.0.

4. The method according to claim 1, wherein the biological sample is a living cell.

5. The method according to claim 1, wherein said mRNA sequence has been altered so as to increase the frequency of said at least one predetermined codon pair.

6. The method according to claim 1, wherein each tRNA of said at least one first tRNA FRET pair corresponds to a tRNA from the complete set of isoacceptor tRNAs specific for the cognate amino acid of said each tRNA, and wherein said at least one first tRNA FRET pair is a first tRNA and a second tRNA, such that, said first tRNA and said second tRNA recognize an adjacent codon pair in said mRNA.

7. The method according to claim 1, further comprising the steps of:

(iv) introducing into the biological sample at least one second tRNA FRET pair capable of reading at least one second codon pair occurring in the mRNA sequence encoding said protein of interest at a frequency that is relatively higher, as compared to the frequency of the at least one second codon pair in the proteome or transcriptome; wherein one tRNA member of each at least one second tRNA pair is labeled with a donor fluorophore and the other tRNA member is labeled with an acceptor fluorophore;

(v) detecting FRET signals emitted from the biological sample, thereby measuring translation of the protein of interest.

8. The method according to claim 1, further comprising a step of analyzing the FRET signals emitted from the biological sample, by computing the number of events (N) over a period of time t, wherein $$N \sim \frac{\sum I_t^2}{\sum \delta I_t^2}$$

wherein $I_t$ is the average signal strength at time t and $\delta I_t$ is the average signal deviation at time t, thereby diagnostic a condition selected from the group consisting of a disease, a disorder and a pathological condition.

9. The method according to claim 8, wherein said condition is selected from the group consisting of Fragile X syndrome, autism, aging, memory degeneration, a malignant condition, a pre-malignant condition, a mitochondria-related disease, cardiac hypertrophy, restenosis, diabetes, obesity, genetic disease related to premature termination codons (PTC), and inflammatory bowel disease.

10. A method of evaluating the effect of a drug candidate on the rate of translation of a protein of interest, the method comprising:

(i) providing a first biological sample comprising a protein of interest;

(ii) introducing into the first biological sample at least one first tRNA FRET pair capable of reading a first codon pair occurring in the mRNA sequence encoding said protein of interest at a frequency that is relatively higher, as compared to the frequency of the first codon pair in the proteome or transcriptome; wherein one tRNA member of the at least one tRNA pair is labeled with a donor fluorophore and the other tRNA member is labeled with an acceptor fluorophore;

(iii) providing a second biological sample comprising said protein of interest;

(iv) introducing into the second biological sample said at least one first tRNA FRET pair;

(v) introducing a drug candidate to one of the first biological sample and the second biological sample; and (vi) measuring FRET signals emitted from each of the first and second biological samples, wherein a significant difference between the electromagnetic radiation measured in the first and the second biological samples indicates that the drug candidate affects the rate of translation of the protein of interest.

11. The method according to claim 10, wherein the drug candidate is selected from the group consisting of a small molecule, a peptide, an enzyme, a hormone, a biotherapeutic agent and a proteasome inhibitor.

12. The method according to claim 9, wherein the malignant condition is in a hematological cell.

13. The method according to claim 12, wherein the malignant condition is a hematological malignancy.

14. The method according to claim 13, wherein the hematological malignancy is selected from the group consisting of acute lymphoblastic leukemia, acute myelogenous leukemia, chronic myelogenous leukemia, Hodgkin's disease, non-Hodgkin lymphoma, chronic lymphocytic leukemia, diffuse large B-cell lymphoma, follicular lymphoma, mantle cell lymphoma, hairy cell leukemia, marginal zone lymphoma, Burkitt's lymphoma, post-transplant lymphoproliferative disorder, T-cell prolymphocytic leukemia, B-cell prolymphocytic leukemia, Waldenstrom's macroglobulinemia and multiple myeloma.

15. The method according to claim 13, wherein the hematological malignancy is multiple myeloma.

16. The method of claim 4, wherein said cells are mounted onto a carrier.

17. The method of claim 16, wherein said carrier is a microscope glass slide.

18. The method of claim 8, wherein detecting comprises collecting signals using a fluorescent plate reader.

19. The method of claim 8, wherein analyzing comprises deriving one or more parameters selected from average signal strength, average signal deviation and percentage of labelled tRNA of a given species.

* * * * *

```
                        SEQUENCE LISTING

<160> NUMBER OF SEQ ID NOS: 10

<210> SEQ ID NO 1
<211> LENGTH: 10
<212> TYPE: PRT
<213> ORGANISM: ARTIFICIAL SEQUENCE
<220> FEATURE:
<223> OTHER INFORMATION: SYNTHESIZED

<400> SEQUENCE: 1

Glu Gln Lys Leu Ile Ser Glu Glu Asp Leu
1               5                   10

<210> SEQ ID NO 2
<211> LENGTH: 8
<212> TYPE: PRT
<213> ORGANISM: ARTIFICIAL SEQUENCE
<220> FEATURE:
<223> OTHER INFORMATION: SYNTHESIZED

<400> SEQUENCE: 2

Asp Tyr Lys Asp Asp Asp Asp Lys
1               5

<210> SEQ ID NO 3
<211> LENGTH: 5
<212> TYPE: PRT
<213> ORGANISM: ARTIFICIAL SEQUENCE
<220> FEATURE:
<223> OTHER INFORMATION: SYNTHESIZED

<400> SEQUENCE: 3

Arg Tyr Ile Arg Ser
1               5

<210> SEQ ID NO 4
<211> LENGTH: 6
<212> TYPE: PRT
<213> ORGANISM: ARTIFICIAL SEQUENCE
<220> FEATURE:
<223> OTHER INFORMATION: SYNTHESIZED

<400> SEQUENCE: 4

Asp Thr Tyr Arg Tyr Ile
1               5

<210> SEQ ID NO 5
<211> LENGTH: 6
<212> TYPE: PRT
<213> ORGANISM: ARTIFICIAL SEQUENCE
<220> FEATURE:
```

```
<223> OTHER INFORMATION: SYNTHESIZED

<400> SEQUENCE: 5

Thr Asp Phe Leu Tyr Lys
1               5

<210> SEQ ID NO 6
<211> LENGTH: 11
<212> TYPE: PRT
<213> ORGANISM: ARTIFICIAL SEQUENCE
<220> FEATURE:
<223> OTHER INFORMATION: SYNTHESIZED

<400> SEQUENCE: 6

Lys Pro Pro Thr Pro Pro Pro Glu Pro Glu Thr
1               5                   10

<210> SEQ ID NO 7
<211> LENGTH: 11
<212> TYPE: PRT
<213> ORGANISM: ARTIFICIAL SEQUENCE
<220> FEATURE:
<223> OTHER INFORMATION: SYNTHESIZED

<400> SEQUENCE: 7

Tyr Thr Asp Ile Glu Met Asn Arg Leu Gly Lys
1               5                   10

<210> SEQ ID NO 8
<211> LENGTH: 8
<212> TYPE: PRT
<213> ORGANISM: ARTIFICIAL SEQUENCE
<220> FEATURE:
<223> OTHER INFORMATION: SYNTHESIZED

<400> SEQUENCE: 8

Trp Ser His Pro Gln Phe Glu Lys
1               5

<210> SEQ ID NO 9
<211> LENGTH: 9
<212> TYPE: PRT
<213> ORGANISM: ARTIFICIAL SEQUENCE
<220> FEATURE:
<223> OTHER INFORMATION: SYNTHESIZED

<400> SEQUENCE: 9

Met Arg Phe Val Arg Phe Val Arg Phe
1               5

<210> SEQ ID NO 10
<211> LENGTH: 9
<212> TYPE: PRT
<213> ORGANISM: ARTIFICIAL SEQUENCE
<220> FEATURE:
<223> OTHER INFORMATION: SYNTHESIZED

<400> SEQUENCE: 10

Met Phe Arg Val Phe Arg Val Phe Arg
1               5
```